United States Patent
Sabacinski et al.

(10) Patent No.: US 12,100,283 B2
(45) Date of Patent: Sep. 24, 2024

(54) SYSTEM AND METHOD FOR PERSONAL PROTECTIVE EQUIPMENT

(71) Applicant: 3M INNOVATIVE PROPERTIES COMPANY, St. Paul, MN (US)

(72) Inventors: Richard J. Sabacinski, Charlotte, NC (US); Alyssa W. Sabolis, Midland, NC (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 18/005,747

(22) PCT Filed: Jul. 23, 2021

(86) PCT No.: PCT/IB2021/056674
§ 371 (c)(1),
(2) Date: Jan. 17, 2023

(87) PCT Pub. No.: WO2022/023909
PCT Pub. Date: Feb. 3, 2022

(65) Prior Publication Data
US 2023/0298450 A1 Sep. 21, 2023

Related U.S. Application Data

(60) Provisional application No. 63/058,749, filed on Jul. 30, 2020.

(51) Int. Cl.
*G08B 23/00* (2006.01)
*G08B 21/04* (2006.01)
(Continued)

(52) U.S. Cl.
CPC ......... *G08B 21/0453* (2013.01); *G08B 21/12* (2013.01); *G08B 21/18* (2013.01); *G01N 33/0063* (2013.01)

(58) Field of Classification Search
CPC .... G08B 21/0453; G08B 21/12; G08B 21/18; G01N 33/0063
See application file for complete search history.

(56) References Cited

U.S. PATENT DOCUMENTS 5,065,140 A * 11/1991 Neuburger ......... G01N 33/0062
73/23.31
5,515,723 A * 5/1996 Tsuchida .............. G01N 27/122
73/29.02

(Continued)

FOREIGN PATENT DOCUMENTS

JP 11306463 A 11/1999
JP 2011134214 A 7/2011
(Continued)

OTHER PUBLICATIONS

International Search Report for PCT International Application No. PCT/IB2021/056674, mailed on Oct. 26, 2021, 3 pages.
(Continued)

*Primary Examiner* — Quang Pham

(57) ABSTRACT

A method for use with a personal protective equipment (PPE) article includes determining, via at least one sensor, a first parameter indicative of a concentration of at least one substance in an ambient environment of the PPE article. The method further includes determining, via a processor, a second parameter indicative of a second order derivative of the first parameter with respect to time. The method further includes retrieving, via the processor, a first threshold value indicative of a protection threshold provided by the PPE article for the at least one substance. The method further includes comparing, via the processor, the second parameter with the first threshold value. The method further includes generating, via the processor, an alert signal based on the comparison of the second parameter with the first threshold
(Continued)

value. The method further includes providing, via a user interface, an alert to a user of the PPE article.

20 Claims, 14 Drawing Sheets

(51) Int. Cl.
*G08B 21/12* (2006.01)
*G08B 21/18* (2006.01)
*G01N 33/00* (2006.01)

(56) References Cited

U.S. PATENT DOCUMENTS

| | | | | |
|---|---|---|---|---|
| 6,186,140 | B1* | 2/2001 | Hoague | B01D 46/0091 128/201.25 |
| 6,344,798 | B1* | 2/2002 | Schell | G08B 17/117 73/23.31 |
| 6,472,988 | B1* | 10/2002 | Feld | A62B 9/006 600/534 |
| 6,734,393 | B1* | 5/2004 | Friedl | B23K 9/32 219/130.01 |
| 6,758,081 | B2* | 7/2004 | Schell | F02D 41/144 73/23.31 |
| 7,019,652 | B2* | 3/2006 | Richardson | A62B 9/006 340/517 |
| 8,085,144 | B2* | 12/2011 | Appelt | A61B 5/6814 128/204.23 |
| 8,330,605 | B2* | 12/2012 | Johnson, Jr. | G01N 33/0075 340/3.1 |
| 9,213,016 | B1* | 12/2015 | Stetter | G01N 33/0006 |
| 9,613,525 | B2* | 4/2017 | Boyd | H04L 12/2809 |
| 9,959,735 | B2* | 5/2018 | Patil | H04W 76/10 |
| 10,139,384 | B1* | 11/2018 | Nourbakhsh | G01N 33/0075 |
| 10,488,064 | B1* | 11/2019 | Crowder | F24F 11/52 |
| 10,568,019 | B2* | 2/2020 | Crouthamel | H04W 48/16 |
| 11,740,216 | B2* | 8/2023 | Pratt | G01N 33/0036 205/788 |
| 11,813,926 | B2* | 11/2023 | Varughese | B60H 1/008 |
| 11,828,210 | B2* | 11/2023 | Varughese | F01N 11/00 |
| 11,881,093 | B2* | 1/2024 | Varughese | G08B 17/125 |
| 2003/0000001 | A1* | 1/2003 | McDonald | A62B 7/14 2/6.3 |
| 2004/0004547 | A1* | 1/2004 | Appelt | G08B 21/02 340/539.1 |
| 2006/0085367 | A1* | 4/2006 | Genovese | G06Q 10/00 706/44 |
| 2006/0125623 | A1* | 6/2006 | Appelt | A61B 5/1112 340/521 |
| 2008/0168826 | A1* | 7/2008 | Saidi | G01M 3/20 73/40 |
| 2009/0309744 | A1* | 12/2009 | Fu | G08B 27/006 702/3 |
| 2012/0101411 | A1* | 4/2012 | Hausdorff | A61B 5/1117 600/595 |
| 2013/0174646 | A1* | 7/2013 | Martin | G01N 33/00 73/31.02 |
| 2014/0349707 | A1* | 11/2014 | Bang | G08B 21/12 455/556.1 |
| 2015/0119667 | A1* | 4/2015 | Reihman | A61B 5/7282 600/365 |
| 2017/0193788 | A1* | 7/2017 | Kim | H04W 72/00 |
| 2018/0195977 | A1* | 7/2018 | Hur | G08B 21/14 |
| 2019/0056138 | A1* | 2/2019 | Lee | G06F 16/9038 |
| 2019/0175411 | A1* | 6/2019 | Awiszus | G02F 1/13318 |
| 2020/0027337 | A1* | 1/2020 | Cruz Huertas | G08B 27/003 |
| 2020/0033279 | A1* | 1/2020 | Hur | G08B 21/14 |
| 2020/0126387 | A1* | 4/2020 | Rahman | G08B 21/02 |
| 2020/0168069 | A1 | 5/2020 | Kanukurthy et al. | |

FOREIGN PATENT DOCUMENTS

| | | |
|---|---|---|
| WO | 2020109963 A1 | 6/2020 |
| WO | 2020128952 A2 | 6/2020 |

OTHER PUBLICATIONS

Supplementary European Search Report for EP 21850334.0, 11 pages, dated Jun. 21, 2024.

* cited by examiner

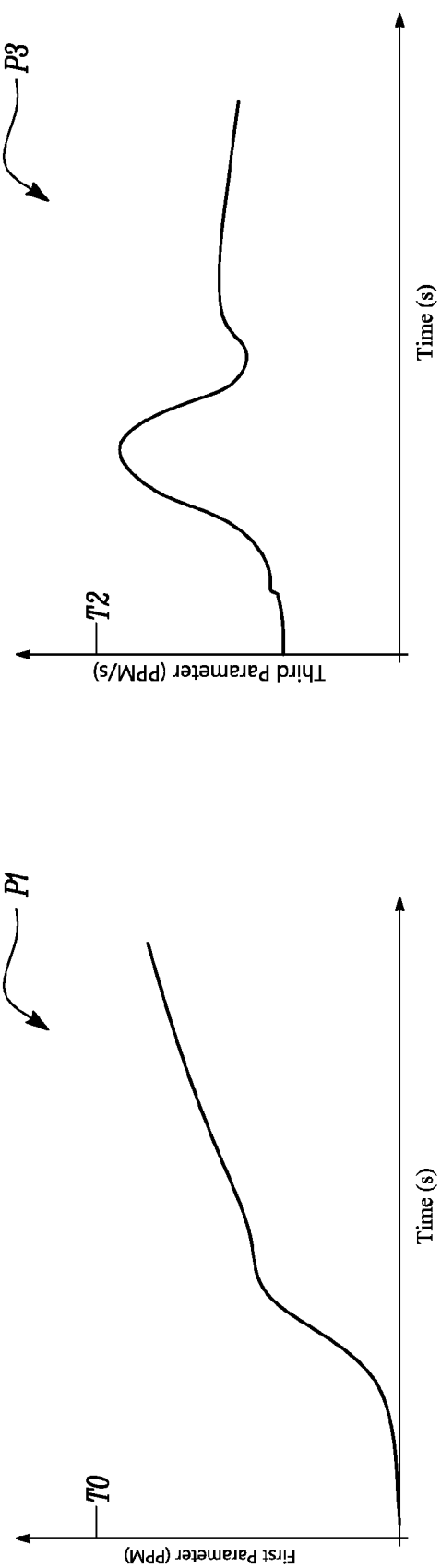
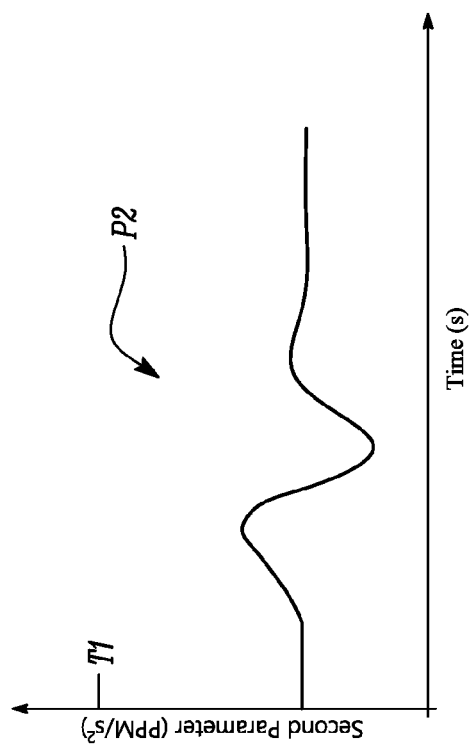
FIG. 12A
FIG. 12B
FIG. 12C

SYSTEM AND METHOD FOR PERSONAL PROTECTIVE EQUIPMENT

TECHNICAL FIELD

The present disclosure relates to a system and a method for use with a personal protective equipment (PPE).

BACKGROUND

Personal protective equipment (PPE) articles may be used by personnel working in hazardous or potentially hazardous environments, for example, chemical environments, biological environments, nuclear environments, fires, etc. Such PPE articles may provide protection against presence or absence of one or more substances in the environment. A wide variety of detectors, sensors and monitors are available to warn about presence of one or more hazardous substances. Such devices may be installed at fixed locations. Such devices may also be hand-held or attached to the PPE article associated with the personnel working in hazardous or potentially hazardous environments. A subsequent alert or warning may be provided to a user for hazardous or potentially hazardous conditions.

Conventional devices may only determine either presence of or a concentration of the one or more substances in the ambient environment. Such devices may not take into account a change in the concentration of the one or more substances and how rapidly the concentration is changing. These indications may be important as the PPE articles may not provide necessary protection if the concentration of the one or more substances is changing at a different rate. Further, the same PPE article may not be effective against the presence or absence of multiple substances (and their corresponding variations in concentrations) in the ambient environment that may expose the personnel to potential safety risks.

SUMMARY

In one aspect, a method for use with a personal protective equipment (PPE) article is described. The method includes determining, via at least one sensor, a first parameter indicative of a concentration of at least one substance in an ambient environment of the PPE article. The method further includes determining, via a processor, a second parameter indicative of a second order derivative of the first parameter with respect to time. The method further includes retrieving, via the processor, a first threshold value indicative of a protection threshold provided by the PPE article for the at least one substance. The method further includes comparing, via the processor, the second parameter with the first threshold value. The method further includes generating, via the processor, an alert signal based on the comparison of the second parameter with the first threshold value. The method further includes providing, via a user interface, an alert to a user of the PPE article based on the alert signal.

In another aspect, a system for use with a personal protective equipment (PPE) article is described. The system includes at least one sensor configured to generate a signal based on a concentration of at least one substance in an ambient environment of the PPE article. The system further includes a processor configured to receive the signal from the at least one sensor. The processor is further configured to determine a first parameter indicative of the concentration of the at least one substance. The processor is further configured to determine a second parameter indicative of a second order derivative of the first parameter with respect to time. The processor is further configured to retrieve a first threshold value indicative of a protection threshold provided by the PPE article for the at least one substance. The processor is further configured to compare the second parameter with the first threshold value. The processor is further configured to generate an alert signal based on the comparison of the second parameter with the first threshold value. The system further includes a user interface configured to provide an alert to a user of the PPE article based on the alert signal received from the processor.

In a further aspect, a method for use with a personal protective equipment (PPE) article is described. The method includes determining, via a plurality of sensors, a plurality of first parameters indicative of concentrations of a plurality of substances in an ambient environment of the PPE article. The method further includes determining, via a processor, a plurality of second parameters corresponding to the plurality of first parameters. Each second parameter is indicative of a second order derivative of the corresponding first parameter with respect to time. The method further includes retrieving, via the processor, a plurality of threshold values corresponding to the plurality of first parameters. Each threshold value is indicative of a corresponding protection threshold provided by the PPE article for the corresponding substance. The method further includes comparing, via the processor, each second parameter with the corresponding threshold value. The method further includes generating, via the processor, an alert signal based on the comparison of each second parameter with the corresponding threshold value. The method further includes providing, via a user interface, an alert to a user of the PPE article based on the alert signal.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

FIGS. 12A-C are graphs illustrating a change in a first parameter, a third parameter and a second parameter with respect to time, in accordance with techniques of this disclosure.

DETAILED DESCRIPTION

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

According to aspects of this disclosure, a method for use with a personal protective equipment (PPE) article includes determining, via at least one sensor, a first parameter indicative of a concentration of at least one substance in an ambient environment of the PPE article. The method further includes determining, via a processor, a second parameter indicative of a second order derivative of the first parameter with respect to time. The method further includes retrieving, via the processor, a first threshold value indicative of a protection threshold provided by the PPE article for the at least one substance. The method further includes comparing, via the processor, the second parameter with the first threshold value. The method further includes generating, via the processor, an alert signal based on the comparison of the second parameter with the first threshold value. The method further includes providing, via a user interface, an alert to a user of the PPE article based on the alert signal.

The first parameter corresponds to a concentration of the at least one substance in the ambient environment. The second parameter corresponds to a change in a rate of change of the concentration of the at least one substance with respect to time. The second parameter may indicate how rapidly the concentration of the at least one substance is changing with time. Through the comparison of the second parameter with the first threshold value, the method may determine if the PPE article is able to provide sufficient protection to the user against the rapid change in the concentration of the at least one substance in the ambient environment. The method may be able to provide advance warning in case of rapid changes in the concentration of the at least one substance.

Figure 1:
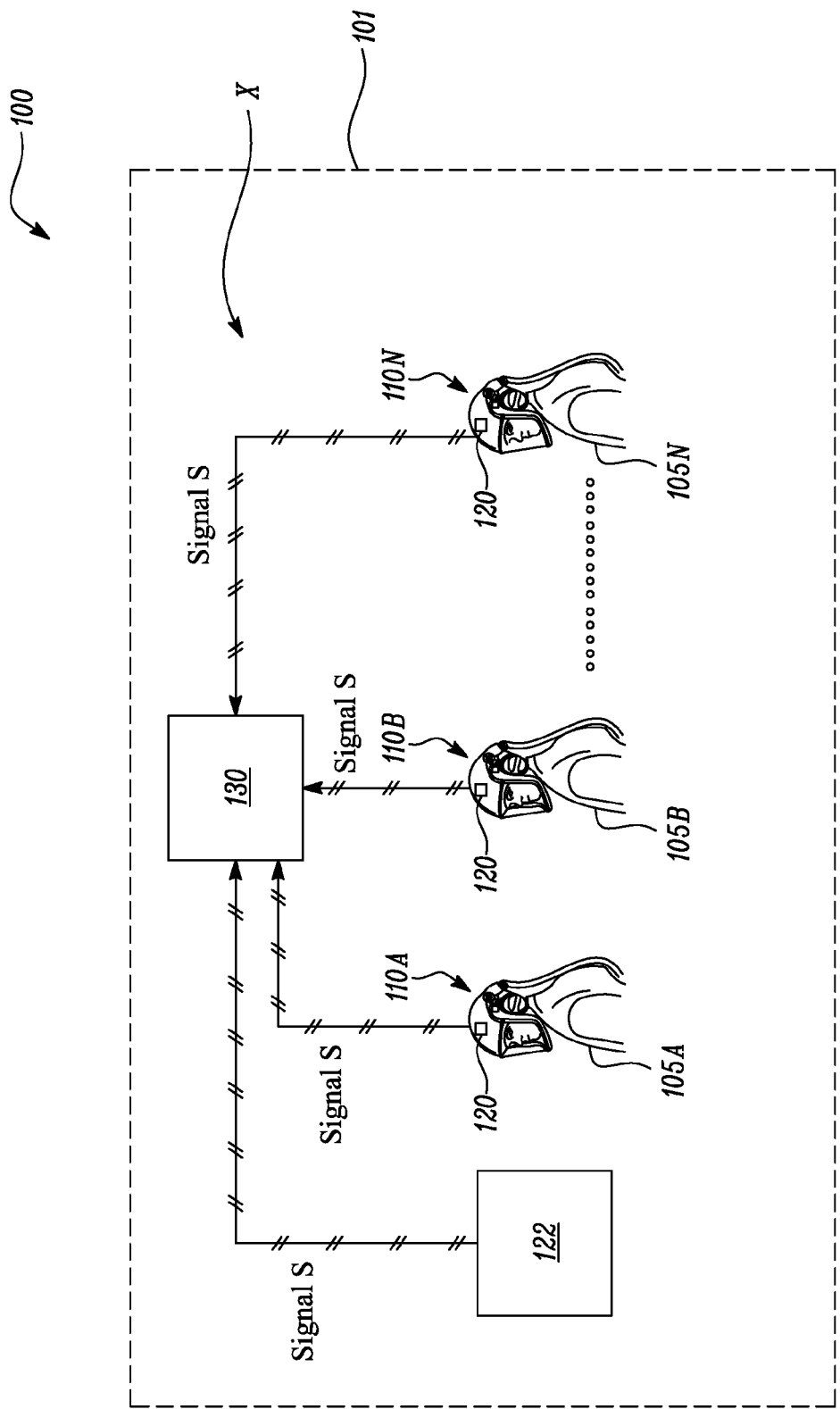
FIG. 1 illustrates a schematic block diagram of an example system for use with one or more personal protective equipment (PPE) articles, in accordance with techniques of this disclosure.

FIG. 1 illustrates a schematic block diagram of an example system 100 for use with personal protective equipment (PPE) articles 110A-110N (collectively, PPE articles 110). The PPE article 110 may be used to protect users 105A-105N (collectively, users 105) from harm or injury from a variety of factors in an ambient environment 101. As used herein, the term "protective equipment" may include any type of equipment or clothing that may be used to protect a user from hazardous or potentially hazardous conditions. In some examples, one or more individuals, such as the users 105, utilize the PPE article 110 while engaging in tasks or activities within the ambient environment 101. In some examples, the PPE articles 110 may be associated with the respective users 105.

Examples of PPE articles 110 may include, but are not limited to, respiratory protection equipment (including disposable respirators, reusable respirators, powered air purifying respirators, self-contained breathing apparatus and supplied air respirators), facemasks, oxygen tanks, air bottles, protective eyewear, such as visors, goggles, filters or shields (any of which may include augmented reality functionality), protective headwear, such as hard hats, hoods or helmets, hearing protection (including ear plugs and ear muffs), protective shoes, protective gloves, other protective clothing, such as coveralls, aprons, coat, vest, suits, boots and/or gloves, protective articles, such as sensors, safety tools, detectors, global positioning devices, mining cap lamps, fall protection harnesses, exoskeletons, self-retracting lifelines, heating and cooling systems, gas detectors, and any other suitable gear configured to protect the users 105 from injury. The PPE articles 110 may also include any other type of clothing or device/equipment that may be worn or used by the users 105 to protect against fire, extreme temperatures, reduced oxygen levels, explosions, reduced atmospheric pressure, radioactive and/or biologically harmful materials.

In some examples, the PPE articles 110 may be used by emergency personnel, for example, firefighters, law enforcement, first responders, healthcare professionals, paramedics, security personnel, or other personnel who work in potentially hazardous conditions, for example, chemical environments, biological environments, nuclear environments, fires, or other physical environments, for example, construction sites, agricultural sites, mining or manufacturing sites.

As used herein, the term "hazardous or potentially hazardous condition" may be used throughout the disclosure to include environmental conditions that may be harmful to a human being, such as high ambient temperatures, lack of oxygen, presence of explosives, exposure to radioactive or biologically harmful materials and exposure to other hazardous substances. Examples of hazardous or potentially hazardous conditions may include, but are not limited to, fire-fighting, biological and chemical contamination clean-ups, explosive material handling, working with radioactive materials and working in confined spaces with limited or no ventilation. The term "hazardous or potentially hazardous conditions" may also be used throughout the disclosure to refer to physiological conditions associated with the users 105, such as heart rate, respiration rate, core body temperature or any other condition which may result in injury and/or death of an individual. Depending upon the type of safety equipment, environmental conditions and physiological conditions, corresponding thresholds or levels may be established to help define hazardous and potentially hazardous conditions.

In some examples, sensors or detectors (e.g., gas detectors) associated with the PPE articles 110 may be installed at fixed locations. Additionally or alternatively, such sensors and detectors may be hand-held or attached to a clothing and/or other safety equipment associated with personnel working in hazardous or potentially hazardous conditions. In some examples, the PPE articles 110 (e.g., respiratory protection equipment) may be worn by the users 105. In some examples, the PPE articles 110 may be a combination of multiple PPE articles 110.

The system 100 includes at least one sensor 120 configured to generate a signal S based on a concentration C of at least one substance X in the ambient environment 101 of the PPE article 110. In some examples, the ambient environment 101 may include the at least one substance X present or absent in the ambient environment 101. In some examples, the at least one sensor 120 may be associated with the PPE articles 110. In some examples, the at least one sensor 120 may be hand-held or attached to a clothing and/or other safety equipment (e.g., a safety helmet, face shield or facemask) associated with the users 105. For example, a gas detector may be associated with a respiratory protection equipment (e.g., self-contained breathing apparatus). In some examples, the at least one sensor 120 may be easily coupled or removed from the PPE articles 110. In some examples, the at least one sensor 120 may be installed at fixed locations, such as a stationary sensor 122. Further, multiple stationary sensors 122 may be installed at different locations in the ambient environment 101.

In some examples, the at least one sensor 120, the stationary sensor 122 and/or the PPE articles 110 may be capable of sending and receiving data by way of one or more wired and/or wireless communication interfaces. For example, the at least one sensor 120 or the stationary sensor 122 may be able to communicate the signal S to the other PPE articles 110 or to a central server 130. In some examples, the ambient environment 101 may include a plurality of wireless access points that may be geographically distributed throughout the ambient environment 101 to provide support for wireless communication throughout the ambient environment 101. In some examples, the at least one sensor 120, the stationary sensor 122 and/or the PPE articles 110 may communicate a corresponding location data with each other and the central server 130.

In some examples, the wireless communication interface may communicate data via one or more wireless communication protocols, such as Bluetooth®, infrared, Wi-Fi, cellular communications network, wireless universal serial bus (USB), radio frequency, near-field communication (NFC), or generally any wireless communication protocol. The central server 130 may generally be enabled to employ any form of machine-readable media for communicating information from one device to another. The central server 130 may include a communication network, including, but not limited to, one or more wireless networks, one or more wired networks, a local area network (LAN), a metropolitan area network (MAN), a wide area network (WAN), a wireless personal area network (WPAN), 802.11, 802.16, 802.20, WiMax networks, a direct connection such as through a Universal Serial Bus (USB) port, and the like, and may include a set of interconnected networks that make up the Internet. In some examples, the wireless network may include, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc.

Examples of the communication network may further include, but are not limited to, a personal area network (PAN), a storage area network (SAN), a home area network (HAN), a campus area network (CAN), an enterprise private network (EPN), Internet, a global area network (GAN), and so forth. Examples are intended to include or otherwise cover any type of network, including known, related art, and/or later developed technologies to connect the central server 130, at least one sensor 120, the stationary sensor 122 and the PPE articles 110 with each other.

In some examples, the at least one substance X may be a hazardous or potentially hazardous substance. In other examples, the at least one substance X may be other substances in the ambient environment 101 (e.g., oxygen) whose absence or low concentration may be hazardous or potentially hazardous. In some example, the at least one substance X may be in any form, such as solid, liquid, gaseous, or plasma. In some examples, the at least one substance X may be either present in the ambient environment 101 (in one or more forms) or appear due to a change in the ambient environment 101, such as leakage, chemical reaction, physical change, or biological change.

As used herein, the term "hazardous or potentially hazardous substance" may include, but not limited to, explosive gases, poisonous gases, biological agents, radionuclides, solid or liquid particles including particulate matter, dust, soot, dirt particles, mist, and/or other gases such as ozone ($O_3$), oxides of nitrogen ($NO_x$), oxides of sulfur ($SO_x$), volatile organic compounds (VOCs), carbon monoxide (CO), hydrogen sulfide ($H_2S$), and/or any other hazardous or potentially hazardous substance. In some examples, the at least one substance X may also include other substances in the ambient environment 101, such as oxygen, carbon dioxide ($CO_2$), water vapors, or generally any gas. In some cases, the hazardous or potentially hazardous substance may include a mixture of two or more substances that are more hazardous or toxic than the individual substances due to synergistic effect.

In the illustrated example, each PPE article 110A-110N is provided with a corresponding sensor 120. However, in some cases, multiple PPE articles 110 may share a single sensor 120. Further, only one stationary sensor 122 is shown. However, any number of stationary sensors 122 may be used as per application requirements.

Figure 2:
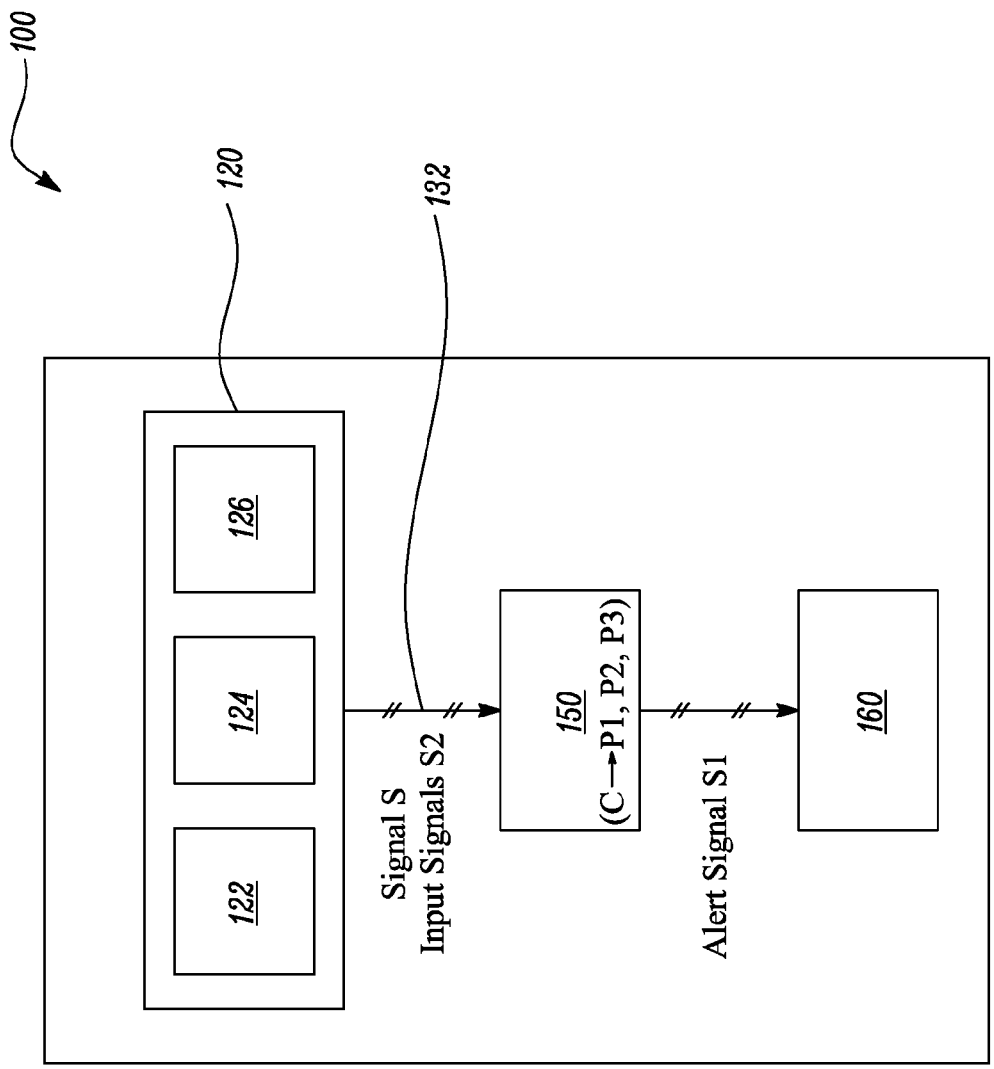
FIG. 2 illustrates a block diagram of an example system for use with a personal protective equipment (PPE) article, in accordance with techniques of this disclosure.

FIG. 2 illustrates a block diagram of an example of the system 100 for use with PPE articles 110. Some components of the system 100 are not shown for the purpose of illustration. Referring to FIGS. 1 and 2, the system 100 includes the at least one sensor 120 configured to generate the signal S based on the concentration C of the at least one substance X in the ambient environment 101 of the PPE article 110. In some examples, the at least one sensor 120 may be configured to generate the signal S periodically with a predetermined time period. In some examples, the at least one sensor 120 may generate the signal S continuously for a predetermined time duration. In other examples, the at least one sensor 120 may continuously generate the signal S.

In some examples, the at least one sensor 120 may be a gas sensor. In other examples, the at least one sensor 120 may be any other type of sensor for determining the concentration C of the at least one substance X including, but not limited to, digital potentiometers, resistive temperature devices (RTD), thermocouples, thermistors, infrared (IR) sensors, pressure detectors, gas detectors, radiation detectors, optical sensors, biohazard detectors, video cameras or any other environmental detector.

In some examples, the at least one sensor 120 may be used to identify, detect and monitor environmental conditions, such as temperature, concentration and flow rate of hazardous substances or other substances (solid/liquid/gaseous) present in the ambient environment 101, biohazards, radionuclides, and/or any other hazardous or potentially hazardous environmental condition. In some examples, the at least one sensor 120 may be used to detect and monitor conditions associated with the PPE articles 110, such as equipment temperature, air supply temperature, air pressure, air flow rate, battery power levels, status of communication interface, and the like. In some examples, the at least sensor 120 may also be used to detect a geo location of the PPE articles 110.

In some examples, the hazardous or potentially hazardous condition may be determined based on the concentration C of the at least one substance X in the ambient environment 101. For example, the hazardous or potentially hazardous condition may arise due to leakage or introduction of the at least one substance X described above in the ambient environment 101. In some examples, the hazardous or potentially hazardous condition may arise due to lack or low concentration of the at least one substance X, for example, oxygen. In some examples, the concentration C of the at least one substance X in the ambient environment 101 may increase, decrease, or remain constant over time. The hazardous or potentially hazardous condition may also be defined based on a rate of change in the concentration C and a change in the rate of change of the concentration C of the at least one substance X in the ambient environment 101.

In some examples, the at least one sensor 120 may include at least one of a portable sensor 124 associated with the PPE article 110, a portable sensor 126 associated with another PPE article (for example, the PPE article 110B) spaced apart from the PPE article (for example, the PPE article 110A), and the stationary sensor 122. In some examples, the portable sensors 124, 126 may be associated with the PPE articles 110, such as a respiratory protection equipment or any other PPE article. The portable sensors 124, 126 and the stationary sensor 122 are able to generate the signal S based on the concentration C of the at least one substance X in their ambient environment 101. Further, the portable sensor 126 associated with another PPE article (for example, the PPE article 110B) may wirelessly communicate the signal S to other PPE articles 110 associated with the users 105 or to the central server 130 (shown in FIG. 1). In some examples, the portable sensors 124, 126, the stationary sensor 122 and/or the PPE articles 110 may be capable of sending and receiving data by way of one or more wired and/or wireless communication interfaces. Further, the at least one sensor 120 and the PPE articles 110 are connected to each other and the central server 130 (shown in FIG. 1) to allow data communication therebetween. In some examples, the stationary sensor 122 may be located at specific locations in the ambient environment 101. Further, multiple stationary sensors 122 may be disposed in the ambient environment 101.

In some examples, the at least one sensor 120 and/or the PPE articles 110 may communicate corresponding location data with each other or the central server 130. In some examples, data communication may occur periodically, for example, every minute. In some examples, the time period between data transmissions may be manually configurable and/or may be automatically configurable by the central server 130. For example, if the central server 130 detects that the at least one sensor 120 and/or the PPE articles 110 have entered the ambient environment 101, the central server 130 may automatically instruct the at least one sensor 120 and/or the PPE articles 110 to transmit the signal S more frequently.

The system 100 further includes a processor 150 configured to receive the signal S from the at least one sensor 120. The signal S may be indicative of the concentration C of the at least one substance X in the ambient environment 101. In some examples, the at least one sensor 120 may be coupled to the processor 150 through a communication link 132. For instance, the communication link 132 may be a physical or a virtual communication channel between the at least one sensor 120 and the processor 150. In some examples, the communication link 132 may represent several wired and/or wireless links. In some examples, the communication link 132 may represent one or more networks and/or direct connections.

In some examples, the processor 150 may be embodied in a number of different ways. For example, the processor 150 may be embodied as various processing means, such as one or more of a microprocessor or other processing elements, a coprocessor, or various other computing or processing devices including integrated circuits such as, for example, an ASIC (application specific integrated circuit), an FPGA (field programmable gate array), or the like. In some examples, the processor 150 may be configured to execute instructions stored in a memory or otherwise accessible to the processor 150. In some examples, the memory may include a cache or random-access memory for the processor 150. Alternatively, or in addition, the memory may be separate from the processor 150, such as a cache memory of a processor, a system memory, or other memory.

As such, whether configured by hardware or by a combination of hardware and software, the processor 150 may represent an entity (e.g., physically embodied in circuitry—in the form of processing circuitry) capable of performing operations according to some embodiments while configured accordingly. Thus, for example, when the processor 150 is embodied as an ASIC, FPGA, or the like, the processor 150 may have specifically configured hardware for conducting the operations described herein. Alternatively, as another example, when the processor 150 is embodied as an executor of software instructions, the instructions may specifically configure the processor 150 to perform the operations described herein.

The processor 150 is configured to determine a first parameter P1 indicative of the concentration C of the at least one substance X. In some examples, the first parameter P1 may correspond to a measured value of the concentration C of the at least one substance X and may change depending upon change in the concentration C of the at least one substance X in the ambient environment 101. Specifically, the measured value corresponding to the concentration C of the at least one substance X may depend upon a type of sensor 120 used. However, the first parameter P1 may be determined irrespective of the type of sensor 120 utilized.

The processor 150 is further configured to determine a second parameter P2 indicative of a second order derivative F2 of the first parameter P1 with respect to time. A first order derivative F1 of the first parameter P1 may correspond to a rate of change of the concentration C of the at least one substance X in the ambient environment 101 with respect to time. The second order derivative F2 may correspond to a change in the rate of change of the concentration C of the at least one substance X with respect to time. In other words, the second order derivative F2 may be obtained by a rate of change of the first order derivative F1 of the first parameter P1. As such, an acceleration/deceleration in the concentration C of the at least one substance X may be obtained through the second order derivative F2 of the first parameter P1. In some examples, such a parameter may indicate if the user 105 may be headed towards a hazardous or potentially hazardous environment or if the at least one substance X may be moving towards the user 105. The second order derivative F2 of the first parameter P1 may indicate how rapidly the change in concentration C of the at least one substance X is occurring in the ambient environment 101. In some examples, the first and second parameters P1, P2 may be determined periodically after a predetermined period of time. In some examples, the first and second parameters P1, P2 may include time averaged measurements for averaging the first and second parameters P1, P2 over a specified interval of time.

The processor 150 is further configured to retrieve a first threshold value T1 indicative of a protection threshold provided by the PPE articles 110 for the at least one substance X. As used herein, the term "protection threshold" may correspond to a threshold level of the PPE articles 110 beyond which it may be unsafe for the users 105 of the PPE articles 110 to be present or work in the ambient environment 101 due to presence, absence or low concentration of the at least one substance X. In some examples, the first threshold value T1 of the PPE articles 110 may indicate the level of protection provided by the PPE articles 110 against the change in the rate of change of the concentration C of the at least one substance X with respect to time in the ambient environment 101. In some examples, the first threshold value T1 may depend upon a type and configuration of the PPE articles 110.

In some examples, multiple first threshold values T1 may be retrieved by the processor 150 corresponding to the presence and concentration C of a particular substance X. In some examples, the first threshold value T1 may be obtained based on government regulations (e.g., occupational safety and health administration exposure limits or American conference of governmental industrial hygienists). Alternatively, the first threshold value T1 may be programmed by an end-user based on application requirements, for example, by an environmental health and safety (EHS) manager.

The processor 150 is further configured to compare the second parameter P2 with the first threshold value T1. In some examples, the processor 150 may compare the second parameter P2 with the first threshold value T1 at different points of time. Specifically, through such a comparison, the processor 150 may be configured to determine if the protection threshold provided by the PPE articles 110 is sufficient to sustain the rapid change in the concentration C of the at least one substance X in the ambient environment 101. This may be determined through the comparison of the second parameter P2 with the first threshold value T1. In some examples, the second parameter P2 may be greater than, less than, or equal to the first threshold value T1. In some examples, the users 105 may be at risk if the concentration C of the at least one substance X surges within a short period of time. In some examples, the users 105 may be at risk if the concentration C of the at least one substance X declines rapidly. For example, the concentration C of the oxygen in the ambient environment 101 may decline rapidly which may be potentially hazardous to the users 105.

In some examples, the processor 150 may be further configured to compare the concentration C of the at least one substance X with a threshold value T0. In some examples, the threshold value T0 may correspond to a concentration of the at least one substance X up to which necessary and sufficient protection may be provided by the PPE articles 110 to the users 105. Specifically, the first parameter P1 may be compared with the threshold value T0.

Figure 3:
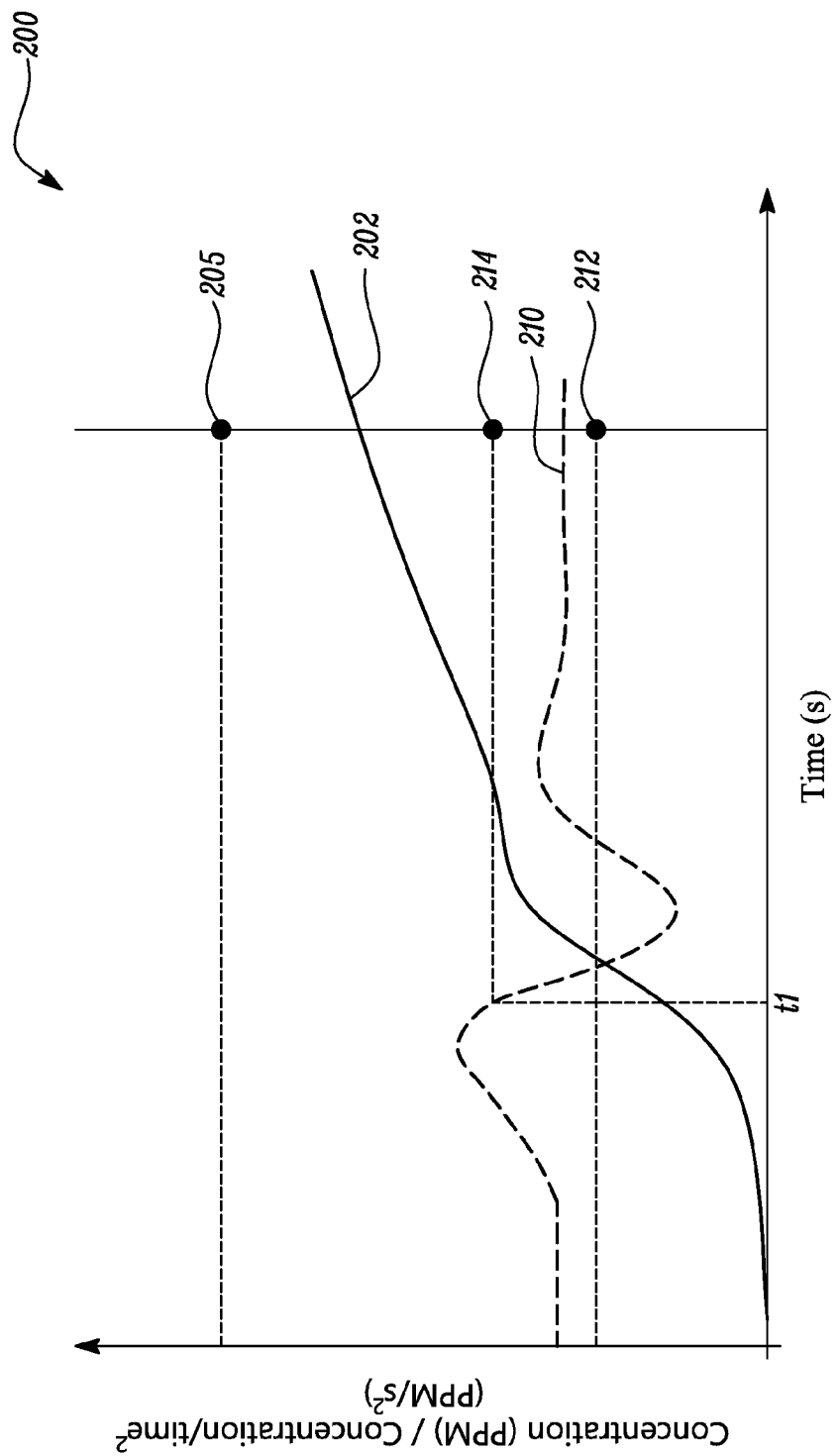
FIG. 3 is a graph illustrating exemplary curves for a change in a concentration and a change in a rate of change of the concentration of at least one substance with respect to time, in accordance with techniques of this disclosure.

FIG. 3 is a graph 200 graph illustrating exemplary curves for a change in the concentration C and a change in a rate of change of the concentration C of the at least one substance X with respect to time. A change in the concentration of the at least one substance X with respect to time is illustrated by a curve 202. In some examples, the curve 202 may be obtained from the signal S received from the at least one sensor 120 (shown in FIG. 2). The first parameter P1 may correspond to the concentration C of the at least one substance X at a given point of time. Hence, the curve 202 may be obtained by plotting values of the first parameter P1 at different points of time. In some examples, the concentration C may be measured in parts per million (PPM) and the time in seconds (s), however, any suitable units may be chosen based on application requirements and a type of the at least one sensor 120 utilized. A change in the rate of change of the concentration C of the at least one substance X with respect to time may be obtained through the second order derivative F2 of the first parameter P1. The change in the rate of change of the concentration C with respect to time at different points of time may be plotted to obtain a second order derivative curve 210. Values along the vertical axis or ordinate of the graph 200 may either be concentration (e.g., PPM) or double derivative of concentration with respect to time (PPM/s$^2$).

Referring to FIGS. 1, 2 and 3, the processor 150 may retrieve the first threshold value T1 corresponding to the protection threshold provided by the PPE articles 110 against the at least one substance X. In some examples, the first threshold value T1 may correspond to a change in the rate of change of the concentration C of the at least one substance X with respect to time up to which the PPE articles 110 may be able to provide the necessary and sufficient protection to the users 105. In some examples, the processor 150 may further retrieve the threshold value T0 corresponding to the concentration C of the at least one substance X up to which the PPE articles 110 may provide sufficient protection to the users 105.

Further, the processor 150 is configured to compare the second parameter P2 with the first threshold value T1 at a given point of time. In the example shown in FIG. 3, the first threshold value T1 and the threshold value T0 are referred to as a first threshold value 212 and a threshold value 205, respectively. A second parameter 214 corresponding to a time t1 is above the first threshold value 212. In other words, the value of the second parameter 214 at time t1 is above the first threshold value 212. Such a comparison may indicate that the PPE article 110 may not be able to provide necessary and sufficient protection to the users 105 against the rapid change in the concentration C of the at least one substance X.

It should be understood that the curves shown in the graph 200 are by way of example only, and the nature of the curves may change based on the variation of the concentration C of the at least one substance X with respect to time. For example, the concentration C of the at least one substance X may increase, decrease, or remain constant over time. Further, the concentration C may change rapidly, slowly, or remain constant over time. In some examples, the first threshold value T1 may vary based on different types and configurations of the PPE articles 110. In some examples, the second parameter 214 may be greater than, less than, or equal to the first threshold value 212.

The processor 150 is further configured to generate an alert signal S1 based on the comparison of the second parameter P2 with the first threshold value T1. In some examples, the processor 150 may be further configured to generate the alert signal S1 if the second parameter P2 is greater than or equal to the first threshold value T1. In some examples, it may be determined that the ambient environment 101 may be unsafe if the second parameter P2 is greater than or equal to the first threshold value T1 and may potentially expose the users 105 to risk. In some examples, processor 150 may be configured to generate the signal S when the second parameter P2 corresponding to the at least one substance X (e.g., oxygen) reaches below the first threshold value T1.

In the illustrated example of FIG. 3, the concentration C of the at least one substance X or the first parameter P1 is below the threshold value 205 at any given point of time. However, the second parameter 214 (at time t1) is above the first threshold value 212. Thus, the processor 150 may generate the alert signal S1 even if the concentration C of the at least one substance X is below the threshold value 205 of the PPE articles 110. Thus, the system 100 may detect a rapid change in the concentration C of the at least substance X even if the concentration C is below the threshold value 205.

In some examples, the alert signal S1 may be generated by the processor 150 if the second parameter P2 reaches a predetermined threshold below the first threshold value T1. For example, the alert signal S1 may be generated if the second parameter P2 reaches 90% of the first threshold value T1. It is to be understood that the predetermined threshold is by way of example only and may vary based on application requirements. In some examples, the predetermined threshold may be configured to be modified by the users 105 or a service technician. In some examples, the alert signal S1 may also be generated to indicate that the ambient environment 101 may be safe for the users 105 of the PPE articles 110.

Figure 4:
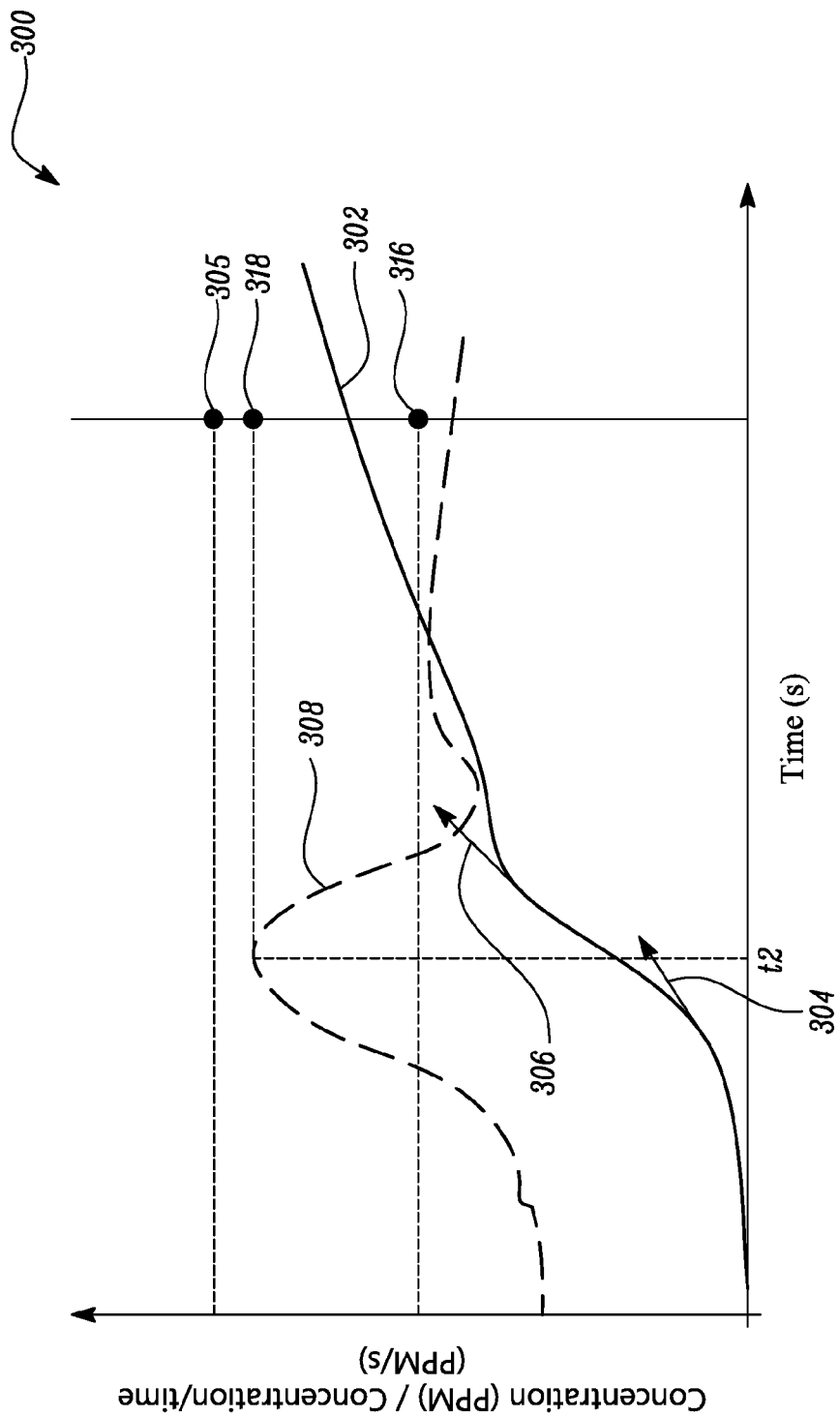
FIG. 4 is a graph illustrating exemplary curves for a change in a concentration and a rate of change of the concentration of at least one substance with respect to time, in accordance with techniques of this disclosure.

FIG. 4 is a graph 300 illustrating exemplary curves for a change in the concentration C and a rate of change of the concentration C of the at least one substance X with respect to time. A change in the concentration of the at least one substance X with respect to time is illustrated by a curve 302. A slope of a tangent line 304 may indicate a rate of change in the concentration C of the at least one substance X at that given point of time. Similarly, the slope of a tangent line 306 may indicate a rate of change in the concentration C of the at least one substance X at another point of time. The slope of such tangent lines (for example, the tangent line 304, 306) at different points of time may be determined to obtain a first order derivative curve 308. In other words, the rate of change of the concentration C of the at least one substance X at different points of time may be plotted to obtain the first order derivative curve 308. Further, the rate of change in the concentration C of the at least one substance X may be obtained through the first order derivative F1 of the first parameter P1. Values along the vertical axis or ordinate of the graph 300 may either be concentration (e.g., PPM) or first derivative of concentration with respect to time (PPM/s).

Referring to FIGS. 1, 2 and 4, the processor 150 may be further configured to determine a third parameter P3 indicative of the first order derivative F1 of the first parameter P1 with respect to time. The third parameter P3 may be indicative of the rate of change in the concentration C of the at least one substance X with respect to time. The processor 150 may retrieve a second threshold value T2 indicative of a protection threshold provided by the PPE articles 110 for the at least one substance X. In some examples, the second threshold value T2 of the PPE articles 110 may indicate the level of protection provided by the PPE articles 110 against the rate of change of the at least one substance X with respect to time in the ambient environment 101. In some examples, the second threshold value T2 may depend upon a type and configuration of the PPE articles 110. Further, the processor 150 may be configured retrieve the threshold value T0 corresponding to the concentration C of the at least one substance X up to which the PPE articles 110 may provide sufficient protection to the users 105.

The second threshold value T2 may or may not be similar to the first threshold value T1. In some examples, the processor 150 may be further configured to compare the third parameter P3 with the second threshold value T2. The processor 150 may periodically compare the third parameter P3 with the second threshold value T2. In the example shown in FIG. 4, the second threshold value T2 and the threshold value T0 are referred to as a second threshold value 316 and a threshold value 305, respectively. A third parameter 318 corresponding to a time t2 is above the second threshold value 316. Specifically, the value of the third parameter 318 at the time t2 is above the second threshold value 316. Such a comparison may indicate that the PPE articles 110 may not be able to provide necessary and sufficient protection to the users 105 against the rate of change in the concentration C of the at least one substance X with respect to time. It should be understood that the curves shown in the graph 300 are by way of example only, and the nature of the curves may change based on the variation of the concentration C of the at least one substance X with respect to time. For example, the concentration C of the at least one substance X may increase, decrease, or remain constant over time.

In some examples, the third parameter P3 may be greater than, less than, or equal to the second threshold value T2. The processor 150 may generate the alert signal S1 further based on the comparison of the third parameter P3 with the second threshold value T2. For example, the processor 150 may generate the alert signal S1 if the third parameter P3 is greater than or equal to the second threshold value T2. In some examples, the processor 150 may generate the alert signal S1 if the third parameter P3 may be less than the second threshold value T2 corresponding to the at least one substance X (e.g., oxygen) in the ambient environment 101.

In the illustrated example of FIG. 4, the concentration C of the at least one substance X or the first parameter P1 is below the threshold value 305 at any given point of time. However, the third parameter 318 (at time t1) is above the second threshold value 316. Thus, the processor 150 may generate the alert signal S1 even if the concentration C of the at least one substance X is below the threshold value 305 of the PPE articles 110.

Figure 5:
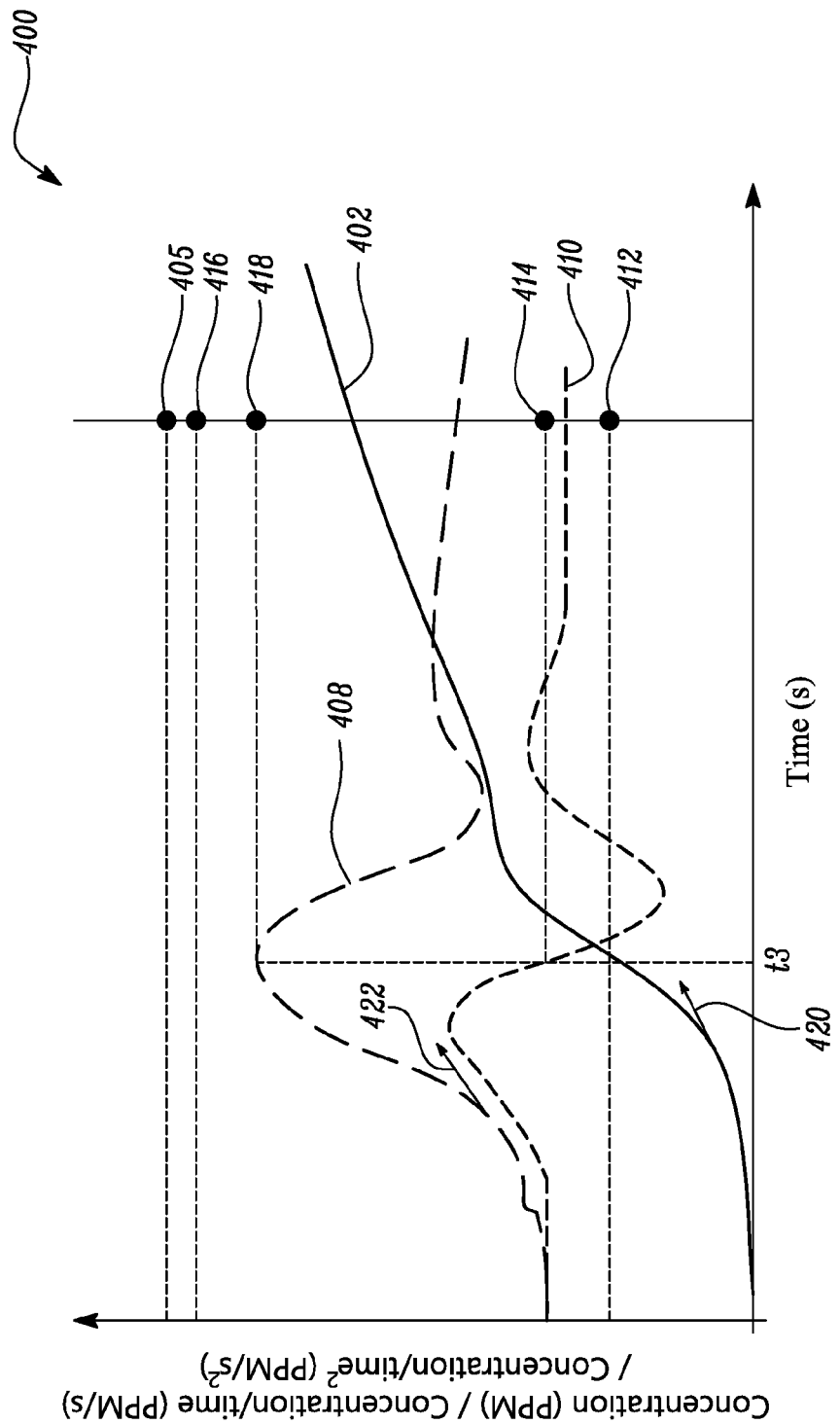
FIG. 5 is a graph illustrating exemplary curves for a change in a concentration, a rate of change of the concentration, and a change in a rate of change of the concentration of at least one substance with respect to time, in accordance with techniques of this disclosure.

FIG. 5 is a graph 400 illustrating exemplary curves for a change in the concentration C, a rate of change of the concentration C, and a change in a rate of change of the concentration C of at least one substance X with respect to time. A change in the concentration of the at least one substance X with respect to time is illustrated by a curve 402. The third parameter P3 or the rate of change in the concentration C of the at least one substance X may be plotted to obtain a first order derivative curve 408. The first order derivative curve 408 may be indicative of a slope of tangent lines (e.g., a tangent line 420) at different points along the curve 402. The second parameter P2 or the change in the rate of change of the concentration C with respect to time at different points of time may be plotted to obtain a second order derivative curve 410. The second order derivative curve 410 may be indicative of a slope of tangent lines (e.g., a tangent line 422) at different points along the curve first order derivative curve 408. Values along the vertical axis or ordinate of the graph 400 may either be concentration (e.g., PPM), first derivative of concentration with respect to time (PPM/s), or second order derivative of concentration with respect to time (PPM/s$^2$).

Referring to FIGS. 1, 2 and 5, the processor 150 may retrieve the second threshold value T2 and the first threshold value T1 corresponding to the rate of change in the concentration C and change in the rate of change of the concentration C, respectively, of the at least one substance X with respect to time. Further, the processor 150 may be configured to receive the threshold value T0 of the PPE articles 110.

In the illustrated example shown in FIG. 5, the second threshold value T2 and the first threshold value T1 are referred to as a second threshold value 416 and a first threshold value 412, respectively. Further, the threshold value T0 is referred to as a threshold value 405. A second parameter 414 corresponding to a time t3 is above the first threshold value 412. In other words, the value of the second parameter 414 at the time t3 is above the first threshold value 412. Even though the third parameter 418 and the concentration C of the at least one substance X are always below the second threshold value 416 and the threshold value 405, respectively, the PPE articles 110 may not be able to provide necessary and sufficient protection to the users 105 against the change in the rate of change of the concentration C of the at least one substance X with respect to time. The processor 150 may generate the alert signal S1 under such conditions. A change in the rate of change of the concentration C may also be taken into account as the PPE articles 110, in some examples, may not be able to withstand a rapid change in the concentration C of the at least one substance X.

In some examples, the processor 150 may be further configured to determine a type of the PPE article 110, and generate the alert signal S1 if the PPE article 110 provides insufficient protection against the at least one substance X. The type of PPE article 110 may be determined by the processor 150 through a unique identifier associated with the PPE article 110. For example, the unique identifier may be any combination of letters, numbers and/or characters associated with a radio frequency identification (RFID) tag, which may communicate with one or more radio frequency readers. In some examples, the user 105 exposure data may be transmitted to a server (e.g., an EHS management server) where PPE records are available against the user data. Further, the processor 150 may determine the type of the PPE article 110 from the central server 130, and correspondingly generate the alert signal S1 if the PPE article 110 provides insufficient protection against the at least one substance X.

In some examples, other information associated with the PPE articles 110 may be obtained by the processor 150, such as, but not limited to, a usage time, an expected life of the PPE articles 110, a component included within the PPE articles 110, a usage history across multiple users of the PPE articles 110, contaminants, hazards, or other physical conditions detected by the PPE articles 110, expiration date of the PPE articles 110, and operating metrics of the PPE articles 110.

Referring again to FIGS. 1 and 2, the system 100 may further include a user interface 160 configured to provide an alert to the users 105 of the PPE articles 110 based on the alert signal S1 received from the processor 150. In some examples, the alert may be generated to indicate to the users 105 of the PPE articles 110 about the hazardous or potentially hazardous condition. Alternatively, the alert may also be generated to indicate a safe environment around the users 105 of the PPE articles 110. In some examples, the system 100 may include multiple user interfaces similar to the user interface 160. In some examples, the users 105 of the PPE articles 110 may generate an alert through the user interface 160, for example, upon determination of a risk. Further, the alert generated by the user 105 may be communicated to the central server 130 or other PPE articles 110 by the processor 150, such that other users 105 may be notified.

In some examples, the alert may include at least one of an audible alert, a visible alert, and a haptic alert. For example, the user interface 160 may include one or more devices to generate audible indication (e.g., one or more speakers), visual indication (e.g., one or more displays, light emitting diodes (LEDs) or the like), or tactile indication (e.g., a device that vibrates or provides other haptic feedbacks). Output components of the user interface 160, in some examples, may include a presence-sensitive screen, a sound card, a video graphics adapter card, speaker, a cathode ray tube (CRT) monitor, a liquid crystal display (LCD), a Light-Emitting Diode (LED), fiber optic indicators, incandescent indicators, a heads-up display, or any other type of device for generating tactile, audio, and/or visual output to a human or machine.

In some examples, a visual alert may be provided by the user interface 160, for example, in the form of green and red indicators, such as light emitting diodes (LEDs) or miniature incandescent lights. In some example, the user interface 160 may be mounted within a peripheral vision of the users 105 of the PPE articles 110, such as, for example, a facemask, helmet, respiratory protection equipment or other protective equipment. The alert provided by the user interface 160 may provide the users 105 of the PPE articles 110 with the necessary time to react to the corresponding hazardous and potentially hazardous conditions and make informed decisions as to whether to proceed or evacuate. This may not only save the users 105 from the risks of hazardous and potentially hazardous conditions, but also, in turn, may save the cost that would otherwise be spent on treatment of the injured users 105 and/or replacing the damaged safety equipment and associated downtime.

In some examples, the alert may include a countermeasure for the users 105 of the PPE articles 110. For example, the countermeasure may include an instruction for the users 105. In some examples, the countermeasure may include an instruction to wear the PPE articles 110. For example, the instruction may indicate the users 105 to wear a particular type of PPE article 110, such as a respiratory protection equipment. In some examples, the instruction may indicate the users 105 to replace the PPE articles 110 with other PPE articles 110. Further, the alert may include an instruction that the PPE articles 110 are no longer required. For example, a visible indication may be turned on when the users 105 are required to wear the PPE articles 110, and the visible indication may be subsequently turned off to indicate that the ambient environment 101 is safe and the PPE articles 110 are no longer required.

In some examples the countermeasure may include an evacuation instruction. For example, the user interface 160 may provide the audible, visible alert and/or the haptic alert to the users 105 of the PPE articles 110 to evacuate the ambient environment 101 as it may be hazardous or potentially hazardous. In some examples, the hazardous or potentially hazardous condition may be determined through the comparison of the second parameter P2 with the first threshold value T1, such that the PPE articles 110 may not be able to provide sufficient protection against the at least one substance X. For example, the ambient environment 101 may become hazardous or potentially hazardous due to rapid change in the concentration C of the at least one substance X. Further, the concentration C of the at least one substance X may increase, decrease, or remain constant with respect to time. In some examples, the countermeasure may include a relocation instruction. For example, the users 105 of the PPE articles 110 may be instructed to relocate to another location that is potentially safe.

In some examples, the processor 150 may be further configured to receive a plurality of input signals S2 from a plurality of sensors 120 disposed at a plurality of locations. The input signals S2 may be indicative of the concentration C of the at least one substance X at the corresponding locations and/or access points. In some examples, the input signals S2 may be received periodically after a predetermined time period. In some examples, the input signals S2 may be received continuously for a predetermined period of time. In other examples, the input signals S2 may be continuously received by the processor 150. In some examples, the input signals S2 may be generated by the plurality of sensors 120 including the portable sensor 124 associated with the PPE articles 110, the portable sensor 126 associated with another PPE article (for example, the PPE article 110B) spaced apart from the PPE article (for example, the PPE article 110A), and the stationary sensor 122 as described earlier.

The processor 150 is further configured to determine an evacuation path based on the input signals S2. In some examples, the evacuation instruction may include the evacuation path. For example, the evacuation path may be determined based on the concentration C of the at least one substance X, the second parameter P2, and the locations of the plurality of sensors 120 disposed at the plurality of locations. In some examples, the evacuation path may be determined based on other factors, such as strength and/or direction of wind. For example, if the wind is blowing in a southerly direction, then the at least one substance X may be likely to move towards the south. The evacuation path may be determined accordingly to avoid an expected trajectory of the at least one substance X.

Alternatively, or in addition, the system 100 may further include a locating device (not shown) configured to generate signals indicative of a location of the PPE articles 110. In some examples, the users 105 of the PPE articles 110 may be restricted to enter the ambient environment 101 due presence of hazardous or potentially hazardous conditions. For example, an alert may be generated through the user interface 160 to indicate the users 105 about the potential risk. In some examples, the user interface 160 may be configured to indicate the concentration C and the location of the at least one substance X in the ambient environment 101.

In some examples, the processor 150 may determine if the users 105 of the PPE articles 110 have not moved for a first predetermined time period when it is determined that hazardous or potentially hazardous conditions exist in the ambient environment 101 of the PPE articles 110. A corresponding alert may be generated through the user interface 160. Further, the users 105 may be allowed to provide inputs to the user interface 160 to stop the alert. In some examples, the processor 150 may communicate an alert to the central server 130 if the location of the user 105 has not changed after a second predetermined time period. In some examples, the second predetermined time period may start after the first predetermined time period. Alternatively, or in addition, the central server 130 may monitor the movement of the users 105 of the PPE articles 110 and may generate an alert signal to be transmitted to the processor 150. Additionally, the central server 130 may monitor exposure of the one or more users 105 of the PPE articles 110 to the at least one substance X.

In some examples, the processor 150 may determine the evacuation path based on input signals from the central server 130. In some examples, the input signals may be obtained from the at least one sensor 120 or other PPE articles 110 in the ambient environment 101. In other examples, the evacuation path may be determined by the central server 130. Alternatively, or in addition, the processor 150 or the central server 130 may utilize historical sensor inputs to determine the evacuation path. In some examples, the central server 130 may generate a substance flow model based on the historical sensor inputs and may use the model to determine the evacuation path. In some examples, an optimum evacuation path may be determined based on the input signals S2. For example, an evacuation path may be computed based on shortest distance from one or more access points or safe locations.

In some examples, the evacuation path may be provided to the users 105 of the PPE articles 110 through the user interface 160. For example, the evacuation path and various directions may be displayed in the form of a map of an area. In some examples, the evacuation path and direction may be displayed in the form of a wind rose graphic. For example, the wind rose may describe the concentration C of the at least one substance X in various directions. This may allow the users 105 to determine a relative location of the source of the at least one substance X and the direction to proceed.

In some examples, the alert may include an end of service life indication of the PPE articles 110. As used herein, the term "service life" of a PPE article may correspond to a period of time after which the disposable parts of a PPE article may need replacement or maintenance is required due to active use. Active use may include exposure to the at least one substance X in the ambient environment 101, power supplied to the device, or electronic or other triggered response to the exposure. For example, power source such as batteries may need replacement from time to time. In some examples, the user interface 160 may provide at least one of an audible alert, a visible alert, and a haptic alert to indicate end of service life of the PPE articles 110.

In some examples, the processor 150 may record the concentration C of the at least one substance X for post analysis and for training personnel. For example, ambient air temperature in a fire fighting environment may be recorded at specified time intervals to provide firefighters or other safety personnel with an understanding of temperature profiles during training or while working within a hazardous site. In some examples, the processor 150 may transmit the data to the central server 130.

Figure 6:
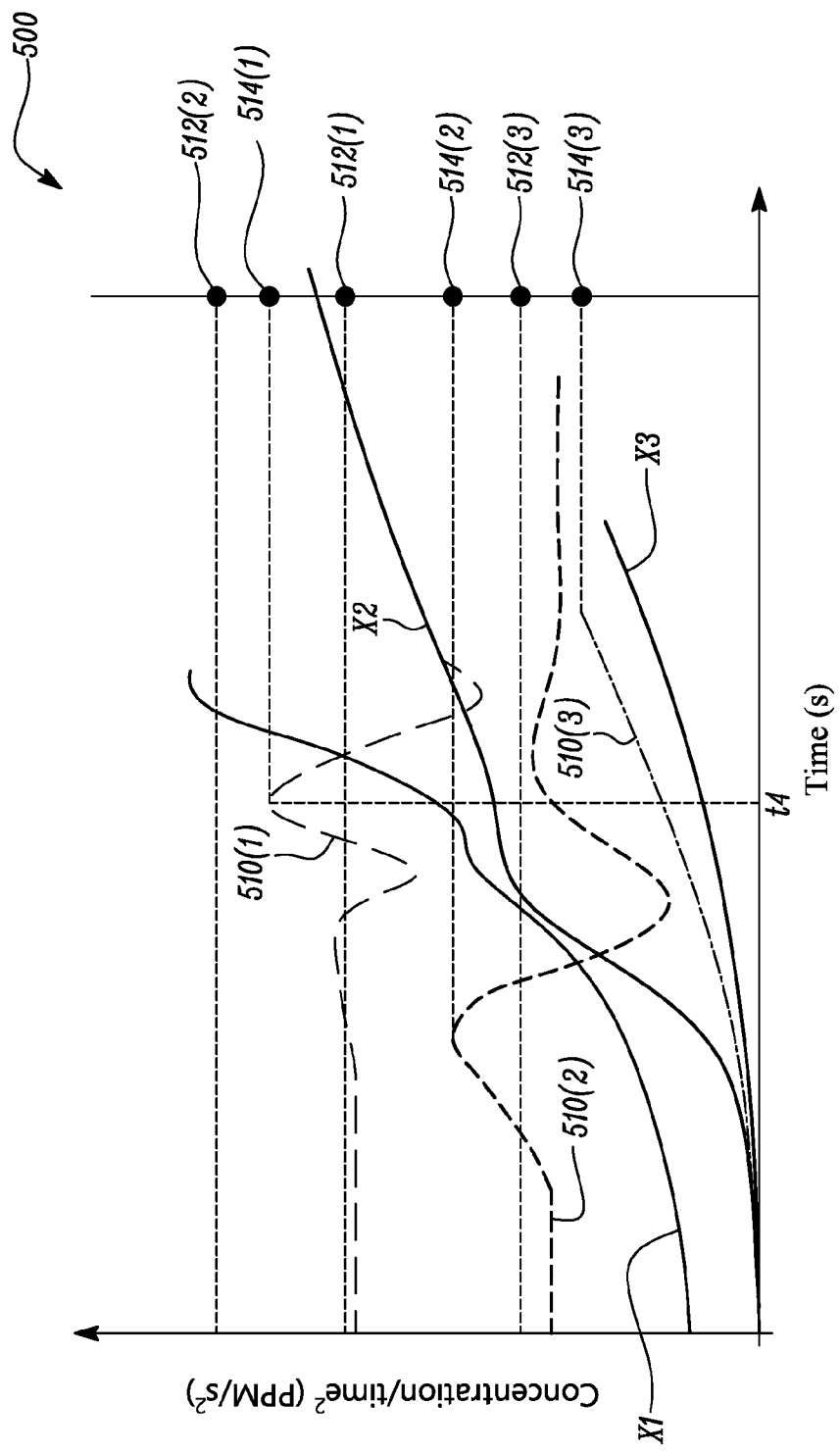
FIG. 6 is a graph illustrating exemplary curves for a change in a rate of change of a concentration of a plurality of substances with respect to time, in accordance with techniques of this disclosure.

FIG. 6 is a graph 500 illustrating exemplary curves for a change in the concentration C1-CN (collectively, concentration C) of a plurality of substances X1-XN (collectively, substance X) with respect to time. In the illustrated example of FIG. 6, three exemplary curves corresponding to substances X1-X3 (i.e., N=3) are shown for illustrative purpose. Referring to FIGS. 1, 2 and 6, the first parameter P1 may include a plurality of first parameters P11-P1N indicative of the concentrations C1-CN of the plurality of substances X1-XN, respectively. For example, the ambient environment 101 may comprise multiple substances X1-XN and each first parameter P1 may correspond to the concentration C of the particular substance X. The processor 150 may be further configured to determine the plurality of first parameters P11-P1N. In some examples, the at least one sensor 120 may generate signals S indicative of the concentrations C1-CN of the plurality of substances X1-XN and the plurality of signals S may be received by the processor 150. In some examples, multiple sensors 120 may generate the plurality of signals S corresponding to the plurality of substances X1-XN. The signals S may be generated intermittently after a predetermined period of time or continuously generated.

In some examples, the processor 150 may be further configured to determine a plurality of second parameters P21-P2N (collectively, second parameter P2) corresponding to the plurality of first parameters P11-P1N. Each second parameter P2 may be indicative of the second order derivative F2 of the corresponding first parameter P1 with respect to time. In some examples, a change in the rate of change of the concentration C of each of the plurality of substances X1-XN with respect to time may be obtained by determining the corresponding second order derivative F2 of the first parameter P1. The change in the rate of change of the concentration C with respect to time at different points of time may be plotted to obtain corresponding second order derivative curves 510(1)-510(N) (collectively, second order derivative curves 510). In the illustrated example of FIG. 3, three second order derivative curves 510(1)-510(3) corresponding to the plurality of substances X1-X3 are shown for illustrative purpose.

In some examples, the processor 150 may be further configured to retrieve a plurality of first threshold values T11-T1N (collectively, first threshold value T1) corresponding to the plurality of first parameters P11-P1N. In the illustrated example of FIG. 6, the plurality of first threshold values T11-T1N are represented by first threshold values 512(1)-512(N) (collectively, first threshold value 512). Specifically, the first threshold values 512(1)-512(3) correspond to the plurality of substances X1-X3, respectively. Each first threshold value T1 may be indicative of a corresponding protection threshold provided by the PPE articles 110 for the corresponding substance X. For example, each first threshold value T1 may correspond to the change in the rate of change of the concentration C of the corresponding substance X with respect to time up to which the PPE articles 110 may be able to provide the necessary and sufficient protection to the users 105. Further, in the illustrated example of FIG. 6, the plurality of second parameters P21-P2N are presented by second parameters 514(1)-514(N) (collectively, second parameter 514). Specifically, the second parameters P21-P23 are represented by the second parameters 514(1)-514(3), respectively.

In some examples, one or more first threshold values 512(1)-512(N) corresponding to the plurality of substances X1-XN may be similar to each other. The processor 150 may be further configured to compare each of the plurality of second parameters 514(1)-514(N) with the corresponding first threshold value 512(1)-512(N). Each of the plurality of second parameters 514(1)-514(N) may be greater than, less than, or equal to the corresponding first threshold value 512(1)-512(N). In some examples, the processor 150 may be configured to determine that the ambient environment 101 is unsafe for the users 105 of the PPE articles 110 if at least one second parameter 514 from the plurality of second parameters 514(1)-514(N) is greater than or equal to the corresponding first threshold value 512.

The processor 150 is further configured to generate the alert signal S1 further based on the comparison of each second parameter 514 with the corresponding first threshold value 512. In some examples, the alert signal S1 may be generated when at least one of the second parameters 514(1)-514(N) is greater than the corresponding first threshold value 512(1)-512(N). In the illustrated example, the second parameter 514(1) corresponding to a time t4 is above the first threshold value 512(1), while the second parameters 514(2)-514(3) are below the corresponding first threshold values 512(2)-512(3). In such a condition, the processor 150 is further configured to generate the alert signal S1. Further, the user interface 160 may be configured to provide an alert to the users 105 of the PPE articles 110 based on the alert signal S1 received from the processor 150. Specifically, the user interface 160 may provide an alert that the second parameter 514(1) corresponding to the substance X1 has crossed the corresponding first threshold value 512(1).

In some examples, two or more substances from the plurality of substances X1-XN may create a synergistic effect. For example, the combined effect of a mixture of two or more substances (e.g., X1, X2) from the plurality of substances X1-XN may be potentially more hazardous (due to synergistic effect) than the effect of the two or more substances individually present in the ambient environment 101 (e.g., carbon tetrachloride and ethyl alcohol). In some examples, one or more substance from the plurality of substances X1-XN, that are otherwise non-toxic, may become hazardous or potentially hazardous (potentiation) due to presence or absence of another substance in the ambient environment 101. In some examples, the combined effect of a mixture of two or more substances from the plurality of substances X1-XN may be less hazardous (antagonism) than the two or more substances individually present in the ambient environment 101.

Such effects may also be taken into account by the processor 150 when generating the alert signal S1. For example, the processor 150 may compare relative concentrations of two or more substances (e.g., X1, X2) in a mixture with a corresponding synergistic threshold of the two or more substances and accordingly generate the alert signal S1. In other examples, the processor 150 may generate the alert signal S1 to indicate that the ambient environment 101 needs to be evacuated due to the presence of the two or more substances where synergistic effects data is not available.

Figure 7:
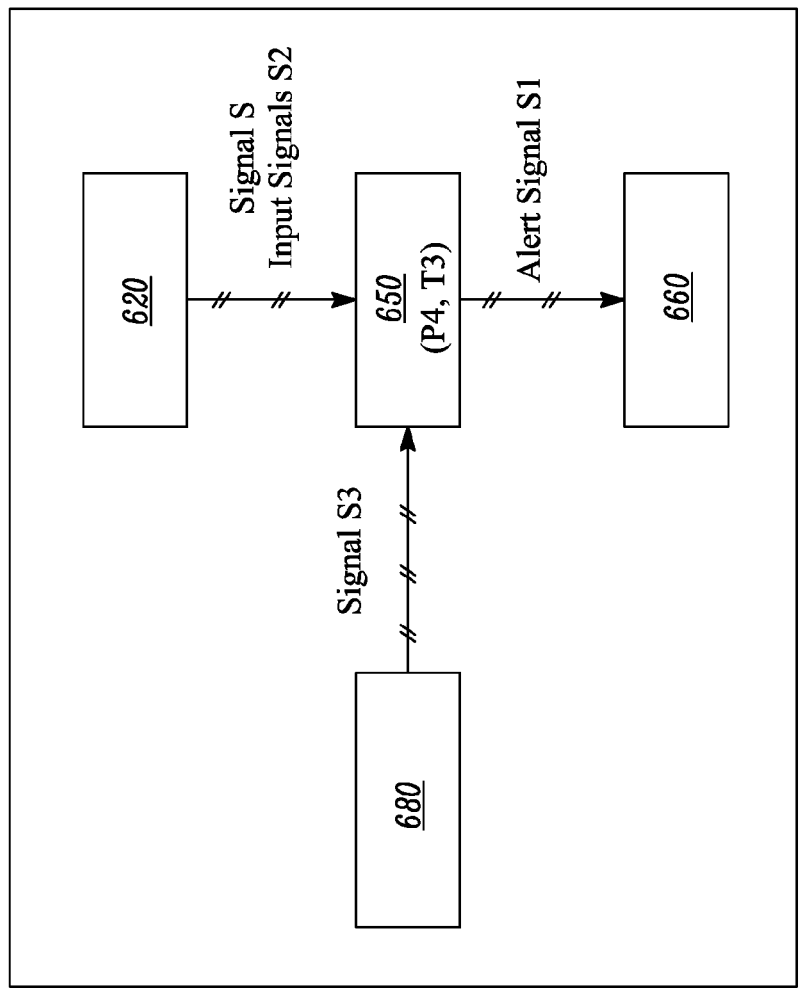
FIG. 7 illustrates a block diagram of an example system for use with a personal protective equipment (PPE) article, in accordance with techniques of this disclosure.

FIG. 7 illustrates a block diagram of an example of a system 600 for use with a personal protective equipment (PPE) article. The system 600 may be similar to the system 100 of FIGS. 1-2 with same or similar corresponding reference numbers. Referring to FIGS. 1-2 and 7, the system 600 includes at least one sensor 620 configured to generate the signal S based on the concentration C of the at least one substance X in the ambient environment 101 of the PPE articles 110. The system 600 further includes a processor 650 configured to receive the signal S from the at least one sensor 620. The system 600 further includes a user interface 660 configured to provide an alert to the users 105 of the PPE articles 110 based on the alert signal S1 received from the processor 650.

The system 600 further includes at least one physiological sensor 680 configured to generate signals S3 based on a physiological condition of the user 105 of the PPE article 110. In some examples, the at least one physiological sensor 680 may generate the signals S3 periodically after a predetermined time period. In some examples, the at least one physiological sensor 680 may generate the signal S3 continuously for a predetermined period of time. In other examples, the at least one physiological sensor 680 may continuously generate the signal S3.

In some examples, the at least one physiological sensor 680 may include, but not limited to, digital potentiometers, resistive temperature devices (RTD), thermocouples, thermistors, infrared (IR) sensors, pressure sensors, gas detectors, radiation detectors, bio-sensors, optical sensors, video cameras or any other physiological sensor. In some examples, the at least one physiological sensor 680 may be disposed on a facemask or other portions of a safety equipment or PPE articles, for example, a helmet, a jacket, a vest, and/or gloves which are worn by the users 105 exposed to hazardous or potentially hazardous conditions.

In some examples, the at least one physiological sensor 680 may be used to monitor various physiological conditions, such as respiration rate, blood oxygen level, core body temperature, heart rate and/or any other physiological conditions required to identify, monitor, and evaluate the physiological condition of the users 105 of the PPE articles 110. The physiological condition may result in injury and/or death of an individual, for example, due to personal overexertion or overheating. In some examples, the at least one physiological sensor 680 may be used to monitor a movement or a lack of movement by the users 105 and/or an equipment associated with the users 105.

In some examples, a hazardous or potentially hazardous condition may be a combination of environmental and physiological conditions associated with the users 105. Depending upon the PPE articles 110, environmental and physiological conditions, corresponding protection thresholds or levels may be established to help define hazardous and potentially hazardous conditions. Exposure to hazardous or potentially hazardous condition may lead to increased use of medication and/or medical emergencies. Health effects may include coughing, wheezing, shortness of breath, aggravated asthma, lung damage (including decreased lung function and lifelong respiratory disease), and premature death in individuals. Individuals with preexisting heart or lung diseases may be more vulnerable. Some substances released in the air, such as benzene or vinyl chloride, are highly toxic and may cause cancer, birth defects, long term injury to the lungs, as well as brain and nerve damage. Further, in some cases, breathing these chemicals may even cause death.

In some examples, the processor 650 may be further configured to determine a physiological parameter P4 indicative of a physiological condition of the user 105 of the PPE article 110 based on the signals S3 received from the at least one physiological sensor 680. In some examples, the processor 650 may be further configured to compare the physiological parameter P4 with a physiological threshold T3 of the user 105. The physiological parameter P4 may be greater than, less than, or equal to the physiological threshold T3 of the user 105. For example, the processor 650 may determine if the user 105 may be in hazardous or potentially hazardous condition based on the comparison of the physiological parameter P4 with the physiological threshold T3 of the user 105. In some examples, the physiological parameter P4 may also vary due to the presence, absence, or low concentration of the at least one substance X in the ambient environment 101. The processor 650 may be further configured to generate the alert signal S1 further based on the comparison of the physiological parameter P4 with the physiological threshold T3. For examples, the processor 650 may generate the alert signal S1 when the physiological parameter P4 is greater than or equal to the physiological threshold T3.

Figure 8:
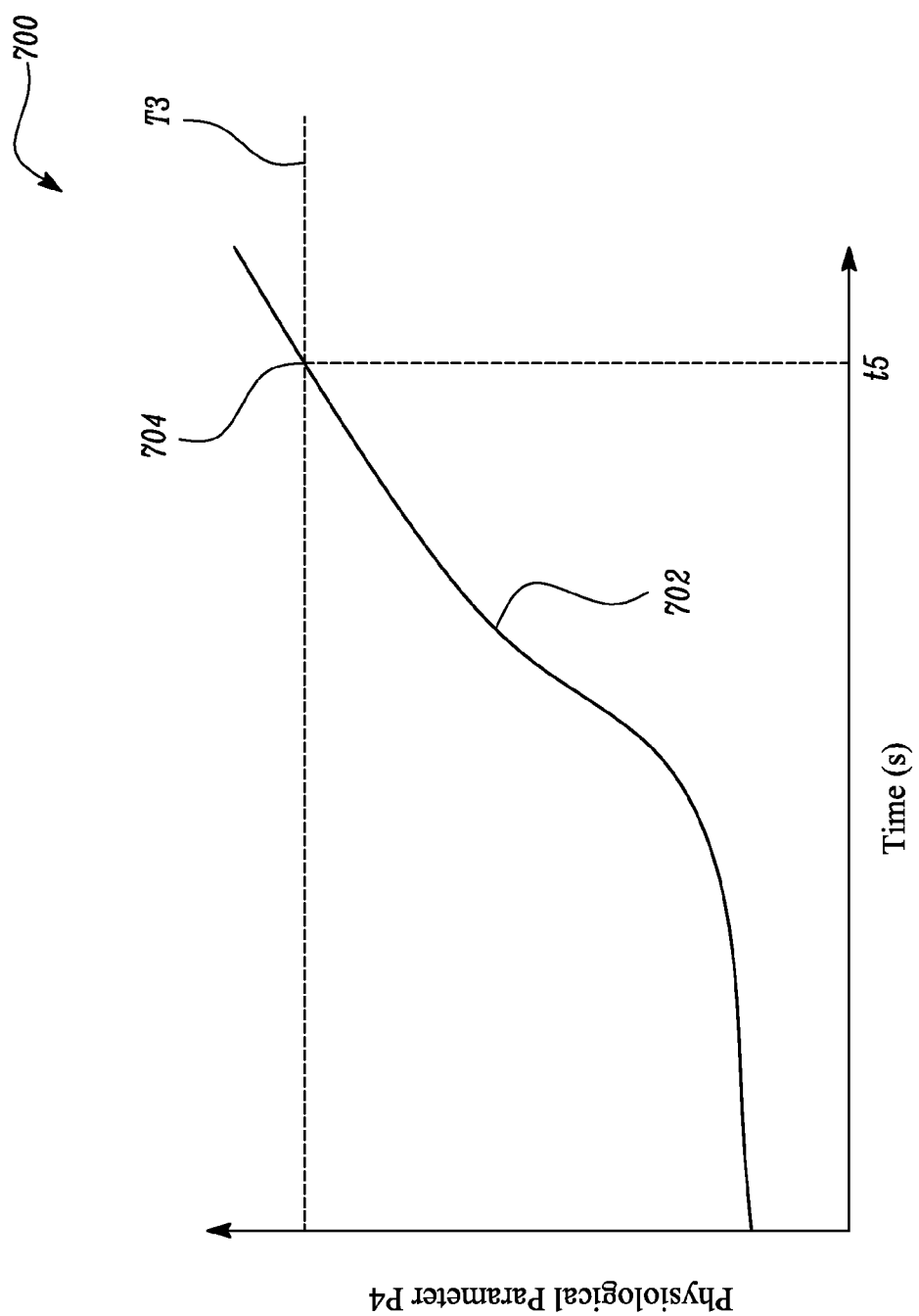
FIG. 8 is graph illustrating an exemplary curve for a change in physiological parameter of a user with respect to time, in accordance with techniques of this disclosure.

FIG. 8 is a graph 700 illustrating an exemplary curve 702 describing a change in the physiological parameter P4 of the user 105 with respect to time. In the illustrated example of FIG. 8, a physiological parameter 704 at a given time t5 is equal to the physiological threshold T3 of the user 105. Thus, the processor 650 (shown in FIG. 7) may generate the alert signal S1. In some examples, the processor 650 may generate the alert signal S1 when the physiological parameter P4 is less than the physiological threshold T3 of the user 105. For example, the physiological parameter P4 may correspond to a blood sugar level of the user 105. It should be understood that the curve 702 and the physiological threshold T3 are by way of example only, and nature of the curve 702 and the values of the physiological threshold T3 may vary based on various conditions.

Referring again to FIG. 7, the processor 650 may generate the alert signal S1 when the physiological parameter P4 reaches a predetermined threshold below the physiological threshold T3 of the user 105. For example, the alert signal S1 may be generated when the physiological parameter P4 reaches 90% of the physiological threshold T3 of the user 105. In some examples, the physiological threshold T3 may be modified by the user 105 or a service technician based on a profile of the user 105. For example, the physiological threshold T3 of the user 105 may vary based on a health condition of the user 105. In some examples, the user interface 660 may be configured to provide an alert to the user 105 of the PPE article 110 based on the alert signal S1 received from the processor 650.

Figure 9:
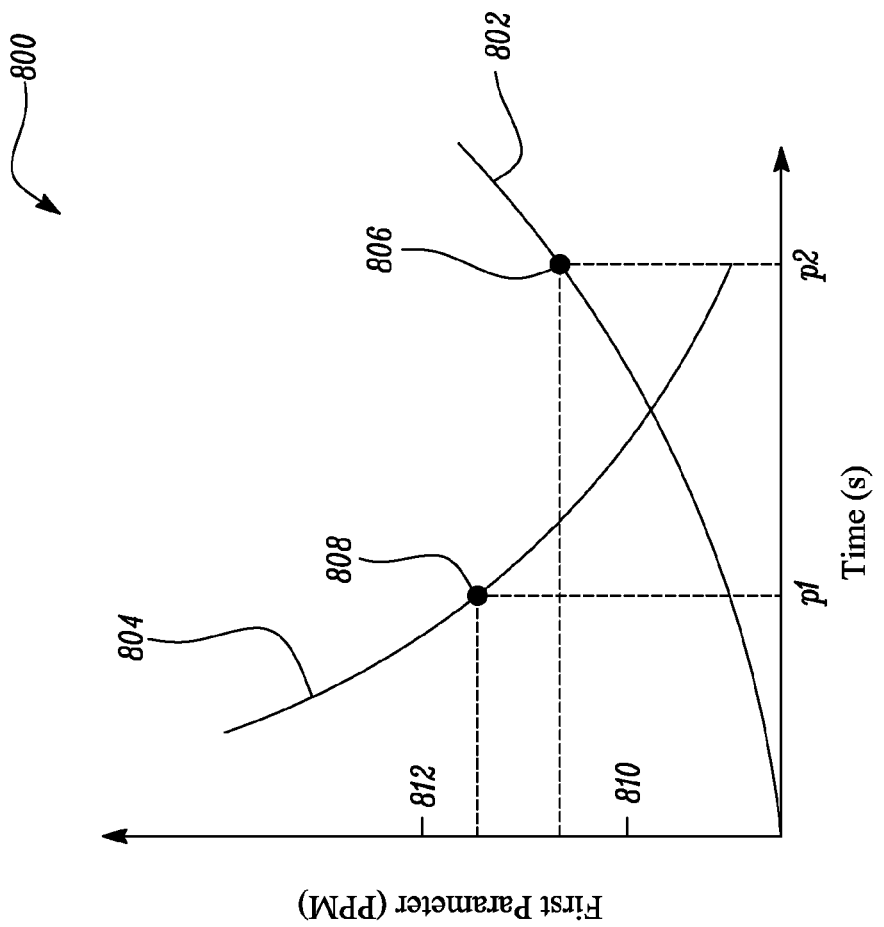
FIG. 9 is a graph illustrating exemplary curves for a change in a first parameter of two substances with respect to time, in accordance with techniques of this disclosure.

FIG. 9 is a graph 800 illustrating exemplary curves for the change in the first parameter P1 of two substances 802, 804 with respect to time. A first parameter 806 corresponds to a concentration Ci of the substance 802 and a first parameter 808 corresponds to a concentration Cj of the substance 804. Further, the first parameter 806 of the substance 802 is increasing with time and the first parameter 808 of the substance 804 is decreasing with time. Referring to FIGS. 1-2 and 9, the threshold value T0 corresponding to the substance 802 and the substance 804 are referred to as a threshold value 810 and a threshold value 812, respectively. The threshold value 810 may correspond to the concentration Ci of the substance 802 up to which necessary and sufficient protection may be provided to the users 105 of the PPE articles 110. The threshold value 812 may correspond to the concentration Cj of the substance 804 above which necessary and sufficient protection may be provided to the users 105 of the PPE articles 110. The substance 804 may be, for example, oxygen, whose concentration Cj is illustrated to be decreasing in the ambient environment 101.

The processor 150 may be configured to compare the first parameter 806 with the corresponding threshold value 810, and the first parameter 808 with the corresponding threshold value 812. In the illustrated example of FIG. 9, at time p2, the first parameter 806 of the substance 802 is greater than the threshold value 810. At time p1, the first parameter 808 of the substance 804 is less than the threshold value 812.

Figure 10:
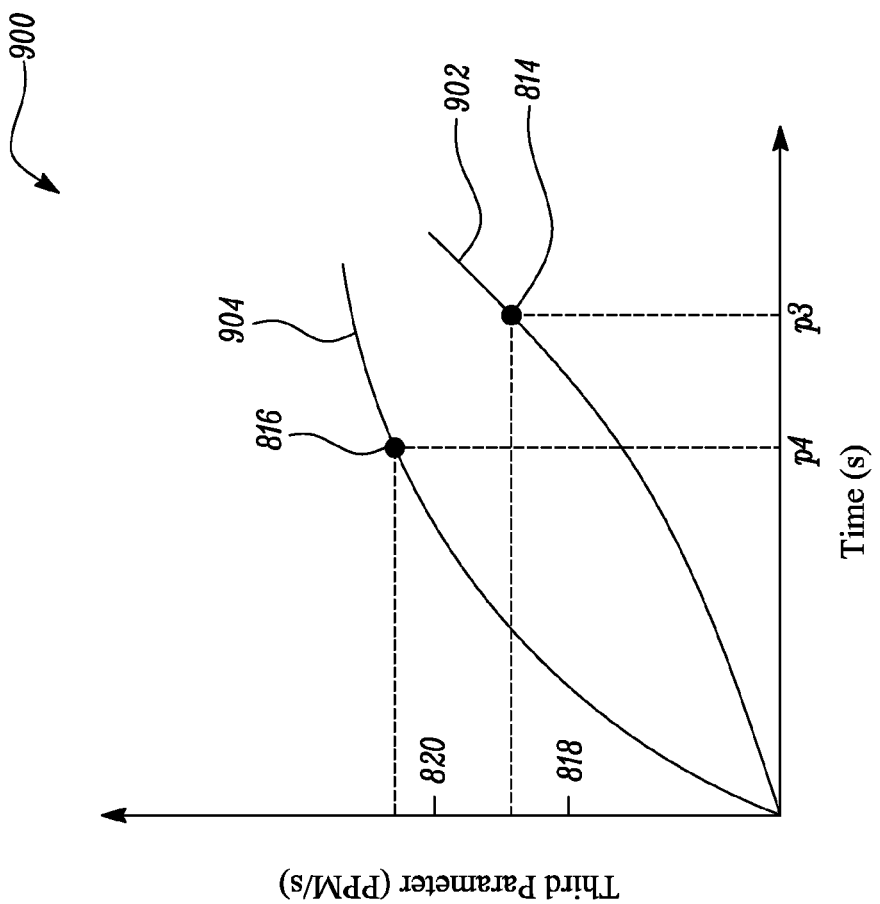
FIG. 10 is a graph illustrating exemplary curves for a change in a third parameter with respect to time of the two substances of FIG. 9, in accordance with techniques of this disclosure.

FIG. 10 is a graph 900 illustrating exemplary curves 902, 904 for a change in the third parameter P3 with respect to time of the two substances 802, 804 of FIG. 9. The third parameter P3 may correspond to the first order derivative F1 of the first parameter P1 with respect to time. Further, the third parameter P3 may correspond to a rate of change in the concentration C of the substance X with respect to time. A third parameter 814 corresponds to a rate of change in the concentration Ci of the substance 802 and a third parameter 816 corresponds to a rate of change in the concentration Cj of the substance 804. In the illustrated example, the third parameters 814, 816 increase with time. Referring to FIGS. 1-2 and 10, the second threshold value T2 corresponding to the substance 802 and the substance 804 are referred to as a second threshold value 818 and a second threshold value 820, respectively. The second threshold values 818, 820 may correspond to a rate of change in the concentrations Ci, Cj of the substances 802, 804 with respect to time up to which necessary and sufficient protection may be provided to the users 105 of the PPE articles 110.

The processor 150 may be configured to compare the third parameter 814 with the corresponding second threshold value 818, and the third parameter 816 with the corresponding second threshold value 820. In the illustrated example of FIG. 10, at time p3, the third parameter 814 of the substance 802 is greater than the second threshold value 818. At time p4, the third parameter 816 of the substance 804 is greater than the second threshold value 820. Referring now to FIGS. 9 and 10, the time p3 is less than the time p2 (p3<p2) and the time p4 is less than the time p1 (p4<p1).

Figure 11:
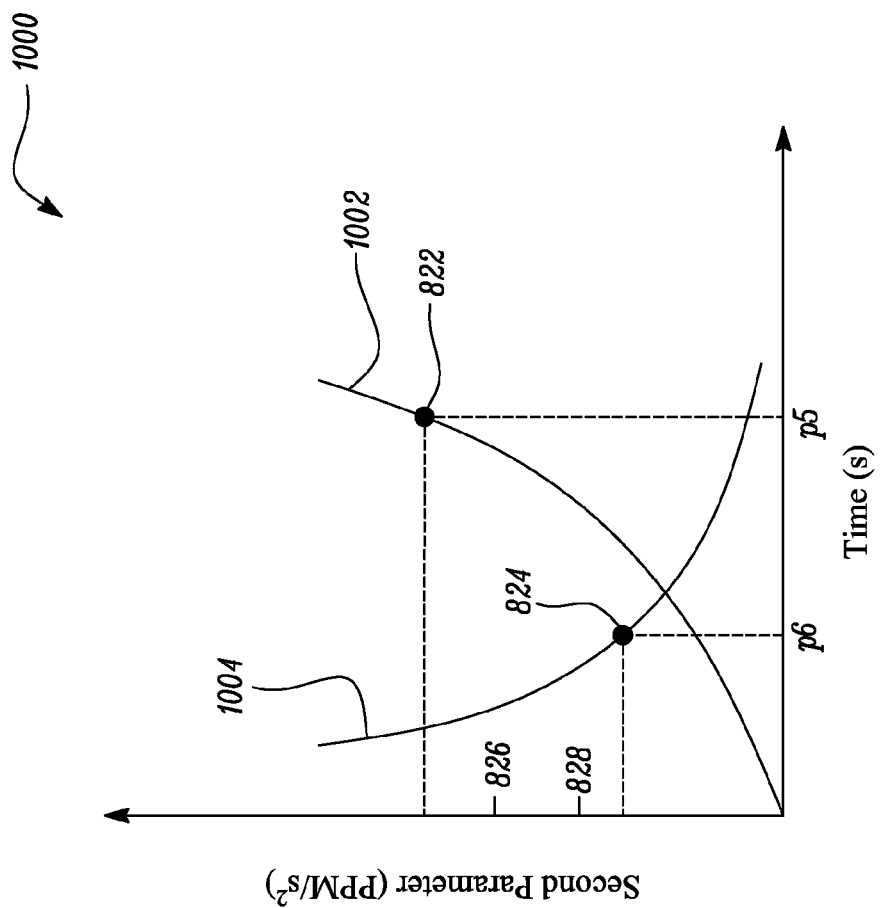
FIG. 11 is a graph illustrating exemplary curves for a change in a second parameter with respect to time of the two substances of FIG. 9, in accordance with techniques of this disclosure.

FIG. 11 is a graph 1000 illustrating exemplary curves 1002, 1004 for a change in the second parameter P2 with respect to time of the two substances 802, 804 of FIG. 9. The second parameter P2 may correspond to the second order derivative F2 of the first parameter P1 with respect to time. Further, the second parameter P2 may correspond to a change in the rate of change of the concentration C of the substance X with respect to time. A second parameter 822 corresponds to a change in the rate of change of the concentration Ci of the substance 802 with respect to time and a second parameter 824 corresponds to a change in the rate of change of the concentration Cj of the substance 804 with respect to time. In the illustrated example, the second parameter 822 corresponding to the substance 802 is increasing with time and the second parameter 824 corresponding to the substance 804 is decreasing with time. Referring to FIGS. 1-2 and FIG. 11, the first threshold value T1 corresponding to the substances 802 and the substance 804 are referred to as the first threshold value 826 and the first threshold value 828, respectively. The first threshold value 826 may correspond to a change in the rate of change of the concentration Ci of the substance 802 with respect to time up to which necessary and sufficient protection may be provided to the users 105 of the PPE articles 110. The first threshold value 828 may correspond to a change in the rate of change of the concentration Cj of the substance 804 with respect to time above which necessary and sufficient protection may be provided to the users 105 of the PPE articles 110.

The processor 150 may be configured to compare the second parameter 822 with the corresponding first threshold value 826, and the second parameter 824 with the corresponding first threshold value 828. In the illustrated example of FIG. 11, at time p5, the second parameter 822 of the substance 802 is greater than the first threshold value 826. At time p6, the second parameter 824 of the substance 804 is less than the first threshold value 828. Referring now to FIGS. 10 and 11, the time p5 is less than the time p3 (p5<p3) and the time p6 is less than the time p4 (p6<p4).

Referring now to FIGS. 1-2 and FIGS. 9-11, the processor 150 may be configured to generate the alert signal S1 based on the comparison of the second parameters 822, 824 with the respective first threshold values 826, 828. The illustrated examples of FIGS. 9-11 show that the processor 150 may generate the alert signal S1 even before the first parameters 806, 808 reach their respective threshold values 810, 812 and the third parameters 814, 816 reach their respective second threshold values 818, 820. Thus, the second order derivative F2 of the first parameters P1 may have to be taken into account to determine hazardous and potentially hazardous conditions. Specifically, the second parameters 822, 824 may reach their corresponding first threshold values 826, 828 before the first parameters 806, 808 reach their corresponding threshold values 810, 812 and the third parameters 814, 816 reach their corresponding second threshold values 818, 820. This may allow the system 100 to anticipate rapid changes in a concentration of a substance before the concentration crosses a threshold. Therefore, the system 100 may allow users to react before a potentially dangerous condition can occur. It should be understood that the curves shown in FIGS. 9-11 are exemplary and may vary based on the concentration C of the at least one substance X.

FIGS. 12A-C are graphs illustrating a change in the first parameter P1, the third parameter P3 and the second parameter P2 with respect to time, respectively. Specifically, FIG. 12A illustrates the change in the first parameter P1 with respect to time, FIG. 12B illustrates the change in the third parameter P3 with respect to time and FIG. 12C illustrates the change in second parameter P2 with respect to time. Referring to FIGS. 1-2 and FIG. 12A, the first parameter P1 corresponds to the concentration C of the at least one substance X in the ambient environment 101. The concentration C of the at least one substance X may be obtained through the signal S received from the at least one sensor 120 at different points of time. Further, the concentration C of the at least one substance X at different points of time may be plotted to obtain the curve illustrated in FIG. 12A.

In some examples, the processor 150 may be further configured to compare the concentration C of the at least one substance X with the threshold value T0. The threshold value T0 may correspond to a concentration of the at least one substance X up to which necessary and sufficient protection may be provided by the PPE articles 110 to the users 105.

Referring to FIGS. 1-2 and FIG. 12B, the third parameter P3 may correspond to a rate of change in the concentration C of the at least one substance X with respect to time. Further, the rate of change in the concentration C of the at least one substance X at different points of time may be plotted to obtain the curve illustrated in FIG. 12B. The third parameter P3 may correspond to the first order derivative F1 of the first parameter P1 with respect to time.

In some examples, the processor 150 may be further configured to compare the third parameter P3 with the second threshold value T2. The second threshold value T2 may correspond to a rate of change in the concentration C of the at least one substance X up to which necessary and sufficient protection may be provided by the PPE articles 110 to the users 105.

Referring to FIGS. 1-2 and FIG. 12C, the second parameter P2 may correspond to a change in the rate of change of the concentration C of the at least one substance X with respect to time. Further, the change in the rate of change of the concentration C of the at least one substance X at different of points of time may be plotted to obtain the curve illustrated in FIG. 12C. The second parameter P2 may correspond to the second order derivative F2 of the first parameter P1 with respect to time.

In some examples, the processor 150 may be further configured to compare the second parameter P2 with the first threshold value T1. The first threshold value T1 may correspond to a change in the rate of change of the concentration C of the at least one substance X with respect to time up to which necessary and sufficient protection may be provided by the PPE articles 110 to the users 105.

Figure 13:
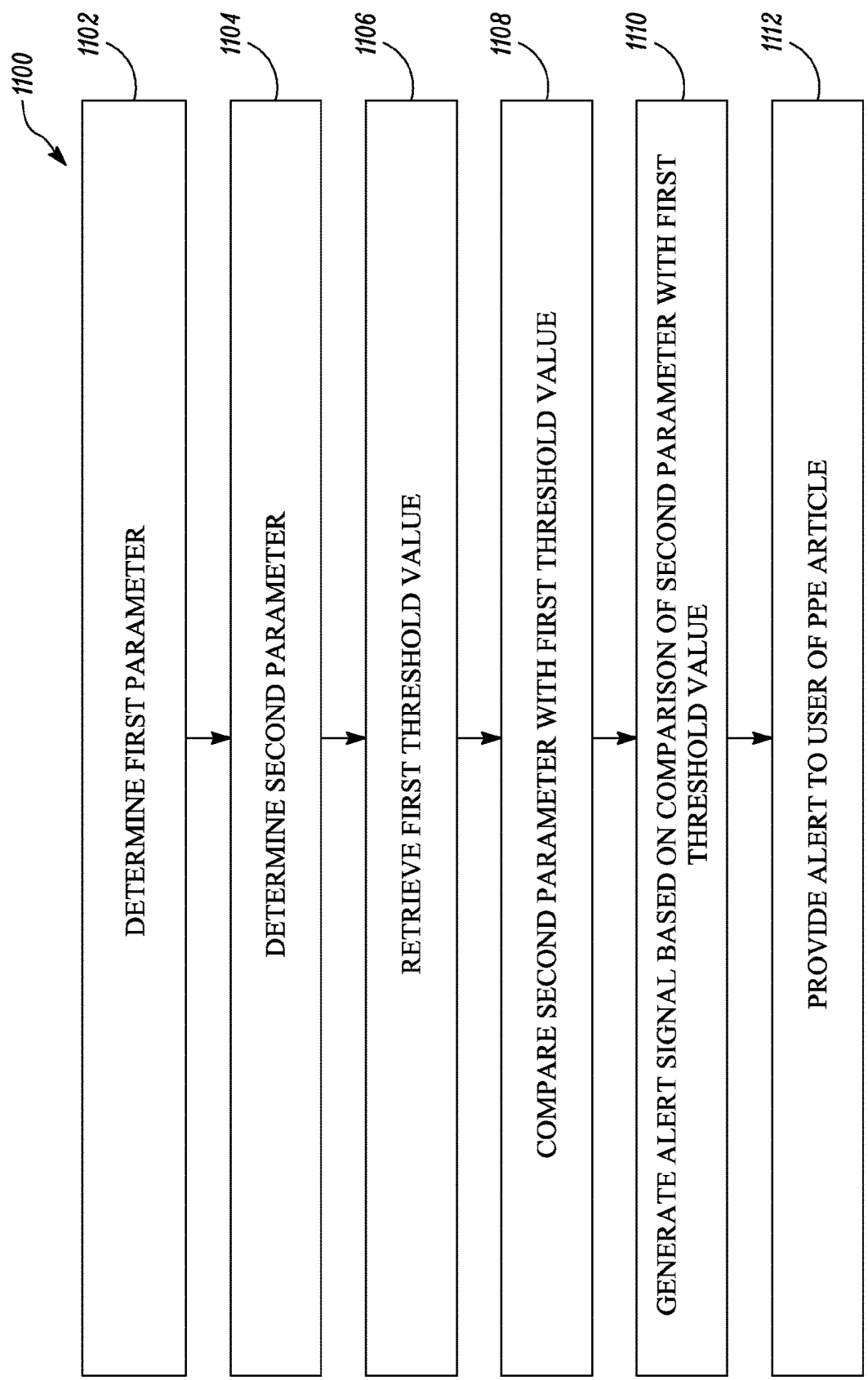
FIG. 13 is a flow chart illustrating a method for use with a personal protective equipment (PPE) article, in accordance with techniques of this disclosure.

FIG. 13 is a flow chart illustrating a method 1100 for use with a personal protective equipment (PPE) article. The method 1100 may be implemented using the systems 100, 600 of FIGS. 1-2 and 7 incorporating the teachings of the present disclosure. At step 1102, the method 1100 includes determining, via the at least one sensor 120, 620, the first parameter P1 indicative of the concentration C of the at least one substance X in the ambient environment 101 of the PPE articles 110. In some examples, the at least one sensor 120, 620 may be a gas sensor. In some examples, the at least one sensor 120, 620 may include at least one of the portable sensor 124 associated with the PPE article 110, the portable sensor 126 associated with another PPE article (for example, the PPE article 110B) spaced apart from the PPE article (for example, the PPE article 110A), and the stationary sensor 122.

At step 1104, the method 1100 further includes determining, via the processor 150, 650, the second parameter P2 indicative of the second order derivative F2 of the first parameter P1 with respect to time. At step 1106, the method 1100 further includes retrieving, via the processor 150, 650, the first threshold value T1 indicative of the protection threshold provided by the PPE articles 110 for the at least one substance X. At step 1108, the method 1100 further includes comparing, via the processor 150, 650, the second parameter P2 with the first threshold value T1. At step 1110, the method 1100 further includes generating, via the processor 150, 650, the alert signal S1 based on the comparison of the second parameter P2 with the first threshold value T1.

In some examples, the method 1100 may further include determining the third parameter P3 indicative of the first order derivative F1 of the first parameter P1 with respect to time. In some examples, the method 1100 may further include comparing the third parameter P3 with the second threshold value T2. In some examples, the alert signal S1 may further be generated based on the comparison of the third parameter P3 with the second threshold value T2.

In some examples, the method 1100 may further include determining, via the at least one physiological sensor 680, the physiological parameter P4 indicative of the physiological condition of the user 105 of the PPE article 110. In some examples, the method 1100 may further include comparing the physiological parameter P4 with the physiological threshold T3. In some examples, the alert signal S1 may further be generated based on the comparison of the physiological parameter P4 with the physiological threshold T3.

In some examples, the method 1100 may further include determining a type of the PPE article 110. In some examples, the alert signal S1 may further be generated if the PPE article 110 provides insufficient protection against the at least one substance X. At step 1112, the method 1100 further includes providing, via the user interface 160, 660, an alert to the users 105 of the PPE articles 110 based on the alert signal S1. In some examples, the alert may be generated if the second parameter P2 is greater than or equal to the first threshold value T1. In some examples, the alert may include at least one of an audible alert, a visible alert, and a haptic alert. In some examples, the alert may include an end of service life indication of the PPE articles 110.

In some examples, the alert may further include providing a countermeasure to the users 105 of the PPE articles 110. In some examples, the countermeasure may include an evacuation instruction. In some examples, the countermeasure may include a relocation instruction.

In some examples, the method 1100 may further include receiving the plurality of input signals S2 from the plurality of sensors 120, 620 disposed at a plurality of locations. In some examples, the input signals S2 may be indicative of the concentration C of the at least one substance X at the corresponding locations. In some examples, the method 1100 may further include determining an evacuation path based on the input signals S2. In some examples, the evacuation instruction may include the evacuation path.

In some examples, the first parameter P1 may include the plurality of first parameters P11-P1N indicative of the concentrations C1-CN of the plurality of substances X1-XN. In some examples, determining the first parameter P1 may further include determining the plurality of first parameters P11-P1N. In some examples, determining the second parameter P2 may further include determining the plurality of second parameters P21-P2N corresponding to the plurality of first parameters P11-P1N. Each second parameter P2 may be indicative of the second order derivative F2 of the corresponding first parameter P1 with respect to time. In some examples, retrieving the first threshold value T1 may further include retrieving the plurality of first threshold values T11-T1N corresponding to the plurality of first parameters P11-P1N. Each first threshold value T1 may be indicative of the corresponding protection threshold provided by the PPE articles 110 for the corresponding substance X.

In some examples, comparing the second parameter P2 with the first threshold value T1 may further include comparing each second parameter P2 with the corresponding first threshold value T1. In some examples, the alert signal S1 may further be generated based on the comparison of each second parameter P2 with the corresponding first threshold value T1.

Figure 14:
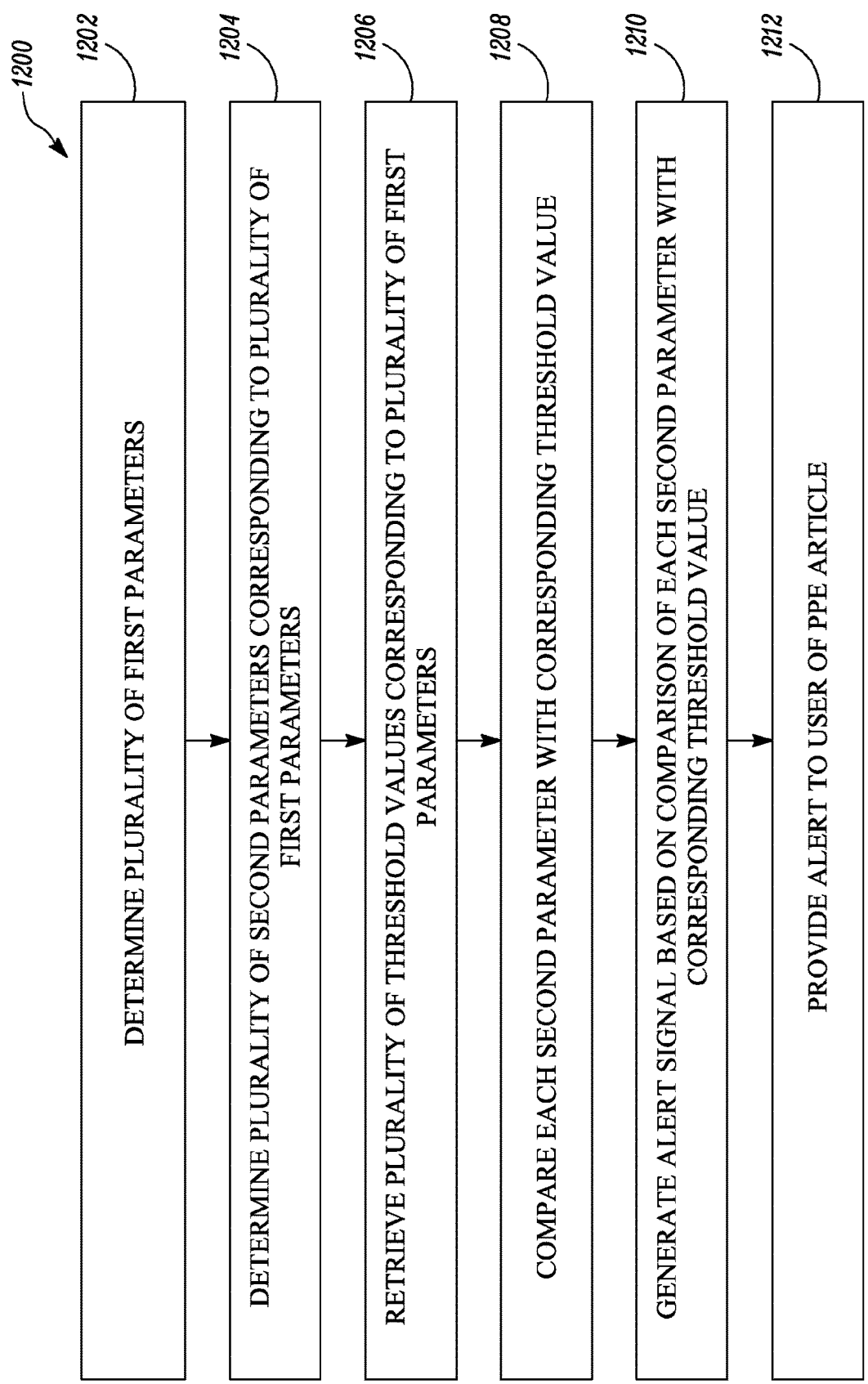
FIG. 14 is a flow chart illustrating a method for use with a personal protective equipment (PPE) article, in accordance with techniques of this disclosure.

FIG. 14 illustrates a flow chart describing a method 1200 for use with a PPE article. The method 1200 may be implemented using the system 100, 600 of FIGS. 1-2 and 7 incorporating the teachings of the present disclosure. At step 1202, the method 1200 includes determining, via the plurality of sensors 120, 620, the plurality of first parameters P11-P1N indicative of the concentrations C1-CN of the plurality of substances X1-XN in the ambient environment 101 of the PPE articles 110. At step 1204, the method 1200 further includes determining, via the processor 150, 650, the plurality of second parameters P21-P2N corresponding to the plurality of first parameters P11-P1N. Each second parameter P2 may be indicative of the second order derivative F2 of the corresponding first parameter P1 with respect to time.

At step 1206, the method 1200 further includes retrieving, via the processor 150, 650, the plurality of first threshold values T11-T1N corresponding to the plurality of first parameters P11-P1N. Each first threshold value T1 is indicative of a corresponding protection threshold provided by the PPE article 110 for the corresponding substance X. At step 1208, the method 1200 further includes comparing, via the processor 150, 650, each second parameter P2 with the corresponding first threshold value T1.

At step 1210, the method 1200 further includes generating, via the processor 150, 650, the alert signal S1 based on the comparison of each second parameter P2 with the corresponding first threshold value T1. At step 1212, the method 1200 further includes providing, via the user interface 160, 660, an alert to the users 105 of the PPE articles 110 based on the alert signal S1.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized, and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below, or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

The invention claimed is:

1. A method for use with a personal protective equipment (PPE) article, the method comprising:
   determining, via at least one sensor, a first parameter indicative of a concentration of at least one substance in an ambient environment of the PPE article;
   determining, via a processor, a second parameter indicative of a second order derivative of the first parameter with respect to time;
   retrieving, via the processor, a first threshold value indicative of a protection threshold provided by the PPE article for the at least one substance;
   comparing, via the processor, the second parameter with the first threshold value;
   generating, via the processor, an alert signal based on the comparison of the second parameter with the first threshold value; and
   providing, via a user interface, an alert to a user of the PPE article based on the alert signal.

2. The method of claim 1, wherein providing the alert further comprises providing a countermeasure to the user of the PPE article.

3. The method of claim 1, wherein the at least one sensor comprises at least one of:
   a portable sensor associated with the PPE article;
   a portable sensor associated with another PPE article spaced apart from the PPE article; and
   a stationary sensor.

4. The method of claim 1, wherein the alert comprises an end of service life indication of the PPE article.

5. The method of claim 1, wherein the alert is generated if the second parameter is greater than or equal to the first threshold value.

6. The method of claim 1, further comprising:
   determining a third parameter indicative of a first order derivative of the first parameter with respect to time; and
   comparing the third parameter with a second threshold value;
   wherein the alert signal is further generated based on the comparison of the third parameter with the second threshold value.

7. The method of claim 1, further comprising:
   determining, via at least one physiological sensor, a physiological parameter indicative of a physiological condition of the user of the PPE article; and
   comparing the physiological parameter with a physiological threshold;
   wherein the alert signal is further generated based on the comparison of the physiological parameter with the physiological threshold.

8. The method of claim 1, further comprises determining a type of the PPE article, wherein the alert signal is further generated if the PPE article provides insufficient protection against the at least one substance.

9. The method of claim 1, wherein:
   the first parameter comprises a plurality of first parameters indicative of concentrations of a plurality of substances;
   determining the first parameter further comprises determining the plurality of first parameters;
   determining the second parameter further comprises determining a plurality of second parameters corresponding to the plurality of first parameters, wherein each second parameter is indicative of a second order derivative of the corresponding first parameter with respect to time;
   retrieving the first threshold value further comprises retrieving a plurality of first threshold values corresponding to the plurality of first parameters, wherein each first threshold value is indicative of a corresponding protection threshold provided by the PPE article for the corresponding substance;
   comparing the second parameter with the first threshold value further comprises comparing each second parameter with the corresponding first threshold value; and
   the alert signal is further generated based on the comparison of each second parameter with the corresponding first threshold value.

10. A system for use with a personal protective equipment (PPE) article, the system comprising:

at least one sensor configured to generate a signal based on a concentration of at least one substance in an ambient environment of the PPE article;

a processor configured to receive the signal from the at least one sensor, the processor configured to:

determine a first parameter indicative of the concentration of the at least one substance;

determine a second parameter indicative of a second order derivative of the first parameter with respect to time;

retrieve a first threshold value indicative of a protection threshold provided by the PPE article for the at least one substance;

compare the second parameter with the first threshold value;

generate an alert signal based on the comparison of the second parameter with the first threshold value; and a user interface configured to provide an alert to a user of the PPE article based on the alert signal received from the processor.

11. The system of claim 10, wherein the alert comprises a countermeasure for the user of the PPE article.

12. The system of claim 10, wherein the alert comprises at least one of an audible alert, a visible alert, and a haptic alert.

13. The system of claim 10, wherein the at least one sensor comprises at least one of:

a portable sensor associated with the PPE article;

a portable sensor associated with another PPE article spaced apart from the PPE article; and a stationary sensor.

14. The system of claim 10, wherein the alert comprises an end of service life indication of the PPE article.

15. The system of claim 10, wherein the processor is further configured to generate the alert if the second parameter is greater than or equal to the first threshold value.

16. The system of claim 10, wherein the processor is further configured to:

determine a third parameter indicative of a first order derivative of the first parameter with respect to time;

compare the third parameter with a second threshold value; and generate the alert signal further based on the comparison of the third parameter with the second threshold value.

17. The system of claim 10, further comprising at least one physiological sensor configured to generate signals based on a physiological condition of the user of the PPE article, wherein the processor is further configured to:

determine a physiological parameter indicative of a physiological condition of the user of the PPE article based on the signals received from the at least one physiological sensor;

compare the physiological parameter with a physiological threshold; and generate the alert signal further based on the comparison of the physiological parameter with the physiological threshold.

18. The system of claim 10, wherein the processor is further configured to determine a type of the PPE article, and generate the alert signal if the PPE article provides insufficient protection against the at least one substance.

19. The system of claim 10, wherein the first parameter comprises a plurality of first parameters indicative of concentrations of a plurality of substances, and wherein the processor is further configured to:

determine the plurality of first parameters;

determine a plurality of second parameters corresponding to the plurality of first parameters, wherein each second parameter is indicative of a second order derivative of the corresponding first parameter with respect to time;

retrieve a plurality of first threshold values corresponding to the plurality of first parameters, wherein each first threshold value is indicative of a corresponding protection threshold provided by the PPE article for the corresponding substance;

compare the second parameter with the first threshold value further comprises comparing each second parameter with the corresponding threshold value; and generate the alert signal further based on the comparison of each second parameter with the corresponding first threshold value.

20. A method for use with a personal protective equipment (PPE) article, the method comprising:

determining, via a plurality of sensors, a plurality of first parameters indicative of concentrations of a plurality of substances in an ambient environment of the PPE article;

determining, via a processor, a plurality of second parameters corresponding to the plurality of first parameters, wherein each second parameter is indicative of a second order derivative of the corresponding first parameter with respect to time;

retrieving, via the processor, a plurality of first threshold values corresponding to the plurality of first parameters, wherein each first threshold value is indicative of a corresponding protection threshold provided by the PPE article for the corresponding substance;

comparing, via the processor, each second parameter with the corresponding first threshold value;

generating, via the processor, an alert signal based on the comparison of each second parameter with the corresponding first threshold value; and providing, via a user interface, an alert to a user of the PPE article based on the alert signal.

* * * * *